(12) United States Patent
Zech

(10) Patent No.: US 9,606,099 B2
(45) Date of Patent: Mar. 28, 2017

(54) SELECTION DEVICE

(71) Applicant: Josef Zech, Innsbruck (AT)

(72) Inventor: Josef Zech, Innsbruck (AT)

( * ) Notice: Subject to any disclaimer, the term of this patent is extended or adjusted under 35 U.S.C. 154(b) by 0 days.

(21) Appl. No.: 14/411,863

(22) PCT Filed: Jul. 2, 2013

(86) PCT No.: PCT/EP2013/063932
§ 371 (c)(1),
(2) Date: Dec. 29, 2014

(87) PCT Pub. No.: WO2014/006043
PCT Pub. Date: Jan. 9, 2014

(65) Prior Publication Data
US 2015/0192561 A1    Jul. 9, 2015

(30) Foreign Application Priority Data

Jul. 2, 2012 (EP) .................................. 12174599

(51) Int. Cl.
*B01L 3/00* (2006.01)
*G01N 33/483* (2006.01)
(Continued)

(52) U.S. Cl.
CPC .......... *G01N 33/4833* (2013.01); *B01L 3/502* (2013.01); *B01L 3/56* (2013.01);
(Continued)

(58) Field of Classification Search
CPC ................................................. G01N 33/4833
See application file for complete search history.

(56) References Cited

U.S. PATENT DOCUMENTS 3,659,749 A * 5/1972 Schwartz .......... A61M 5/31596
                                                      222/129
4,557,899 A * 12/1985 Schoonover ....... G01N 33/2847
                                                      422/401
(Continued)

FOREIGN PATENT DOCUMENTS

WO    WO-94/17742    8/1994
WO    WO-00/09648    2/2000
(Continued)

OTHER PUBLICATIONS

EP Communication Under Rule 71(3)-Notice of Intention to Grant dated Mar. 6, 2015 with allowed claims in related EP Patent Application Serial 12174599.6.
(Continued)

*Primary Examiner* — Jyoti Nagpaul
(74) *Attorney, Agent, or Firm* — Foley & Lardner LLP; Christopher C. Bolten; Albert K. Heng

(57) ABSTRACT

Device for spermatozoa selection comprising a first chamber configured to receive a first, seminal fluid; a second chamber configured to receive a second fluid, the second chamber being in fluid communication with the first chamber by means of at least one duct having a first opening to the first chamber and a second opening to the second chamber; and a displacement means adapted to displace at least some of the first, seminal fluid towards the first opening.

16 Claims, 18 Drawing Sheets

(51) Int. Cl.
*C12M 3/00* (2006.01)
*C12M 1/34* (2006.01)
*C12N 5/071* (2010.01)

(52) U.S. Cl.
CPC ............ *C12M 21/06* (2013.01); *C12M 41/46* (2013.01); *C12N 5/0612* (2013.01); *B01L 2300/087* (2013.01)

(56) References Cited

U.S. PATENT DOCUMENTS 5,866,354 A * 2/1999 Froman .................... C12Q 1/02
422/50
2012/0052485 A1 3/2012 Shany et al.

FOREIGN PATENT DOCUMENTS

| WO | WO-01/60968 | 8/2001 |
| WO | WO-03/031564 | 4/2003 |
| WO | WO-2012/032165 | 3/2012 |

OTHER PUBLICATIONS

International Search Report dated Oct. 1, 2014 in Int'l PCT Patent Appl Serial No. PCT/EP2013/063932.

* cited by examiner

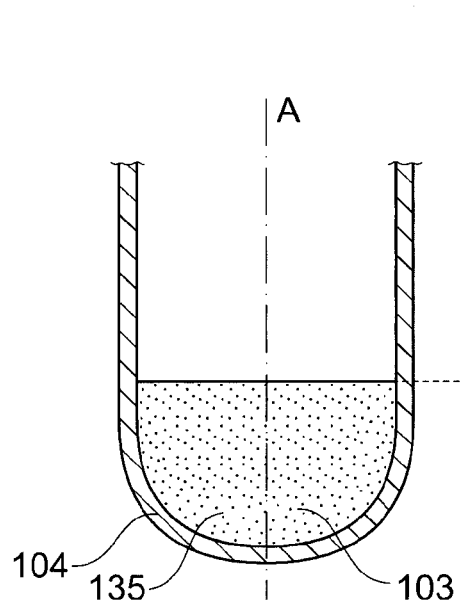
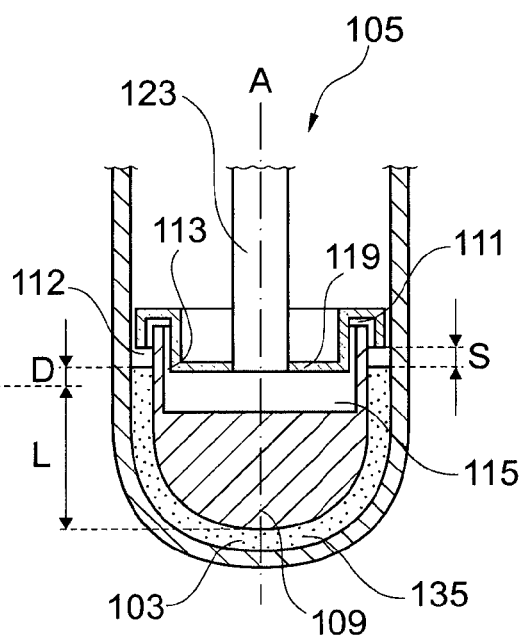
Fig. 7A
Fig. 7B
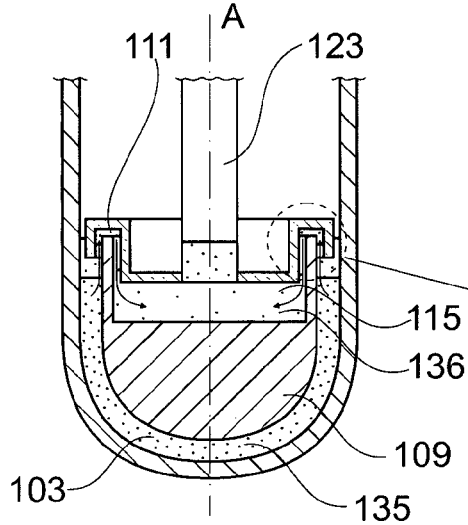
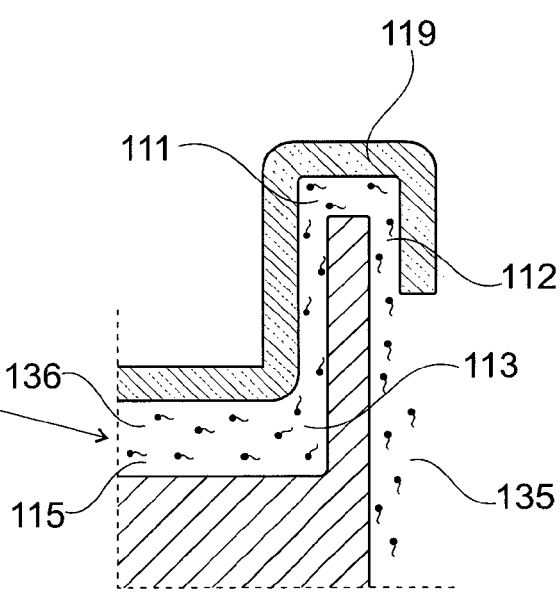
Fig. 7C
Fig. 7D

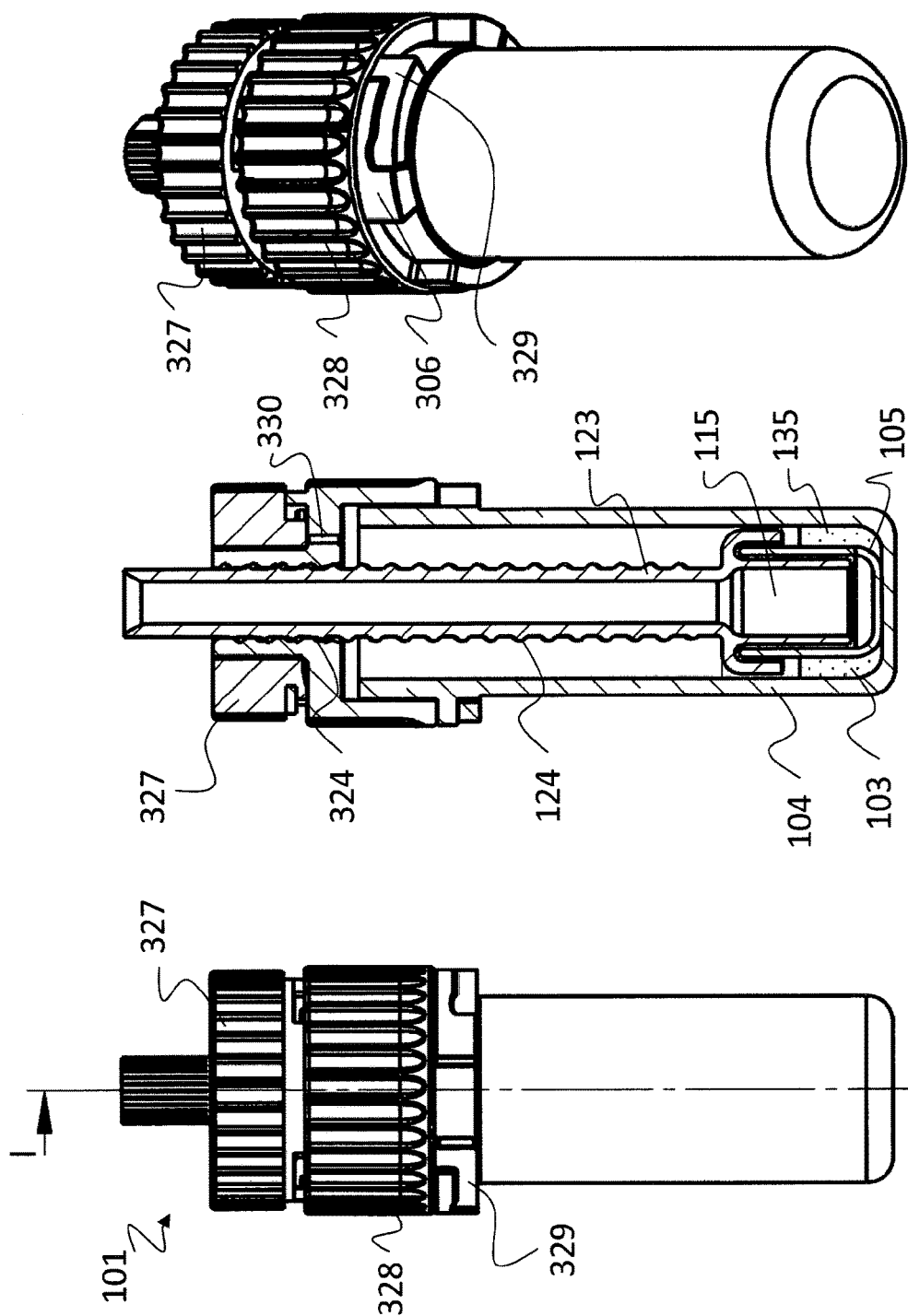

| Donor | Final concentration | |
|---|---|---|
| | Liquefied (Resting time = 15-30 min.) | No liquefication |
| Patient A | 14.9 | 35.12 |
| Patient A | 2.2 | 31.03 |
| Patient A | 9 | 19.93 |
| Patient B | 9.6 | 44.9 |
| Patient C | 3.5 | 32.4 |
| Patient D | 2.5 | 28.4 |

Fig. 16

SELECTION DEVICE

This application is a U.S. national stage filing under 35 U.S.C. §371 of International Patent Application No. PCT/EP2013/063932, filed Jul. 2, 2013, which claims the benefit of EP Patent Application No. 12174599.6, filed Jul. 2, 2012, the entire contents of each of which are incorporated herein by reference.

The present invention relates to a device for spermatozoa selection. More specifically, the present invention relates to a device for spermatozoa selection having a first chamber that is adapted to receive a first, seminal fluid and a second chamber that is adapted to receive a second fluid, the first chamber and the second chamber being fluidly connected by at least one duct. The devices and methods of the present invention can be used to increase the quality of semen samples, and in particular to select and concentrate spermatozoa for motility and/or maturity.

Poor-quality semen samples correlate with failed fertilization, impaired preimplantation development and pregnancy outcome. Factors that negatively contribute to sperm sample quality include meiotic alterations, aneuploidy or sperm DNA damage, particularly sperm DNA fragmentation.

Devices for removing spermatozoa from seminal fluid having a first container and a second container in which a capillary tube provides a liquid bridge between the containers were disclosed by the present inventor in WO-A1 94/17742 and WO-A2 03/031564, the contents of which are hereby incorporated by reference in their entirety.

Figure 1:
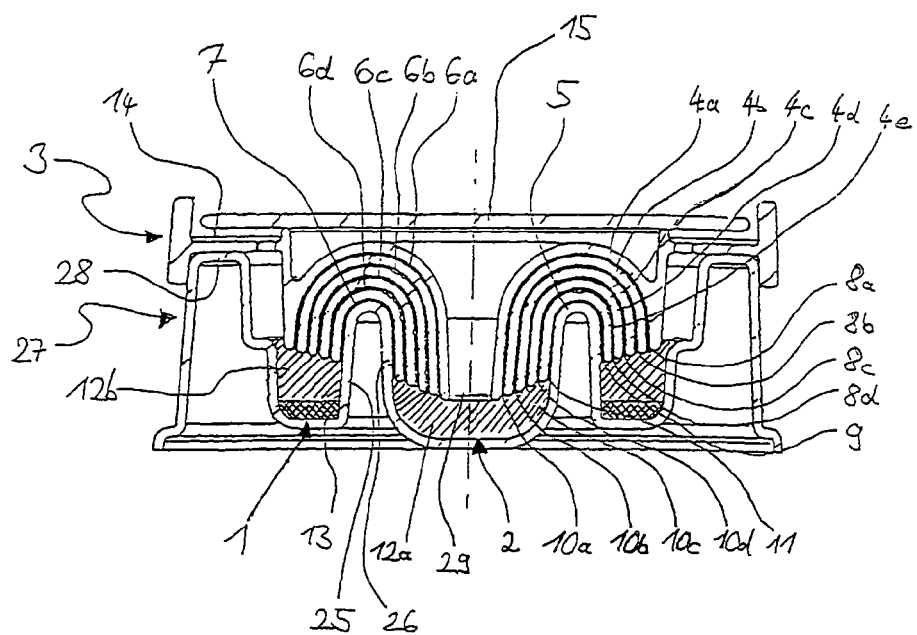
Figure 2:
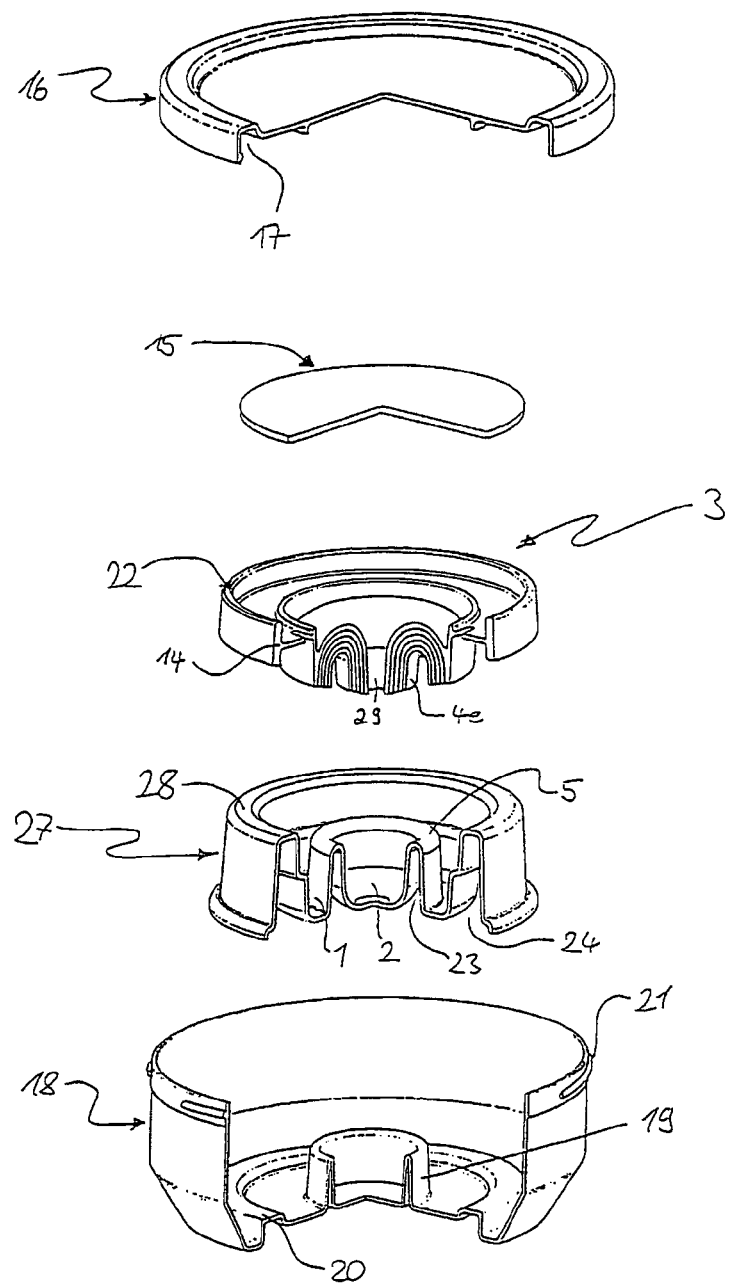

The selection device disclosed in WO-A2 03/031564 is illustrated in FIGS. 1 and 2. As shown, the selection device comprises a first bridge element 3 having four channels 6a-6d and a chamber element 27 having a first ring-shaped chamber 1 for receiving seminal fluid 13 and a second chamber 2 for receiving a medium 12a, the second chamber 12a being connected to the first ring-shaped chamber 1 over a ring-shaped connection 5. The bridge element 3 comprises four boundary walls 4a-4e forming the channels 6a-6d, an additional channel 7 being formed by the boundary wall 4e with the boundary wall of the ring-shaped connection 5 when the bridge element is fitted on the chamber element 27.

As specified in WO-A2 03/031564, selection is performed by filling seminal fluid 13 with spermatozoa into the first ring-shaped chamber 1 such that said seminal fluid does not reach openings 8a-8d and 9 of the channels on the side of the ring-shaped chamber 1 and fitting the bridge element 3 onto the chambers 1, 2. Subsequently, the medium 12a is filled into the chamber 2 over the central opening 29 such that the channels 6a-6d and 7 are filled with medium 12a. Also the seminal fluid 13 in the first ring-shaped chamber 1 may be covered with medium until reaching openings 8a-8d and 9 of the channels on the side of the ring-shaped chamber 1. The channels 6a-6d and 7, therefore, may provide a liquid bridge that is free of currents, allowing the spermatozoa to move through the liquid bridges formed by channels 6a-6d and 7 into the medium in the central chamber 2.

As discovered by the present inventor, the quality of spermatozoa collected in the central chamber 2 of the selection device described above, including spermatozoa yield, is highly dependant upon the volume of seminal fluid filled into the first ring-shaped chamber 1. In particular, the prior selection device is optimized for specific amounts of seminal fluid and smaller volumes have to be compensated by using additional medium. Without being bound by theory, it is believed that the increasing volume of medium required in the first ring-shaped chamber will lead to a lower density of spermatozoa in the central chamber. In this context, it has been discovered that the efficiency of prior art selection devices may be reduced in particular when using seminal fluid volumes of 1 ml or less. Notably, many male patients requiring spermatozoa selection, e.g. for in-vitro fertilization procedures, provide semen samples of 2 ml or less. Also, prior art devices might not function ideally if too much or too little medium is used.

Furthermore, the prior art device disclosed in WO-A2 03/031564 might require spreading the seminal fluid across the surface of the first ring-shaped chamber 1. Without being bound by theory, it is believed that spermatozoa may be mechanically and/or chemically damaged (e.g., due to contact with atmospheric $O_2$) during this procedure, in particular, when attempting to spread small volumes of seminal fluid evenly across the surface of said first ring-shaped chamber 1. It is further believed that higher dilution of the sperm sample may increase the time required for the selection procedure. This might affect spermatozoa quality (e.g., due to chemical damage) and could allow spermatozoa of lower quality to reach the central chamber 2.

Human ejaculate comprises several components such as fluids from the epididymides, fluids from the seminal vesicles, and gland secretions (in particular from the prostate and accessory glands). Since these components are not immediately mixed with each other upon ejaculation and some of them are highly viscid, fresh ejaculate can usually not be suctioned with a needle or a tube. Thus, with current techniques, fresh ejaculate is usually let to rest for 20-30 minutes in order to liquefy it sufficiently for further processing. Again without wanting to be bound by theory, it is believed that spermatozoa may be chemically damaged during this resting period (e.g. due to contact with surrounding $O_2$).

As surprisingly discovered by the present inventor and disclosed in commonly assigned, co-pending WO 2012/032165, the contents of which are hereby incorporated by reference in its entirety, the quality of seminal fluids may be improved substantially by placing a seminal fluid in the first chamber of the above selection device, filing a second chamber of a selection device with a medium for receiving DNA strand break-free spermatozoa and connecting both chambers by a bridge element such that a fluid bridge is formed between the first chamber and the second chamber, which allows the DNA strand break-free spermatozoa to move from said first chamber to said second chamber. However, it has been noted that spermatozoa with strand breaks may be drawn from the first chamber through the fluid bridge when collecting the DNA strand break-free spermatozoa from the second chamber. Without being bound by theory, it is assumed that a slight macroscopic current from the first chamber through the liquid bridge into the second chamber may be caused when the sample is collected.

In view of the above, it is an object of the present invention to provide an improved selection device and a corresponding method that overcomes some or all drawbacks of the prior art. In particular, it is an object of the present invention to provide a selection device and method that can be used with small amounts of seminal fluid.

A further object of the present invention is to provide an improved selection device and method that does not require dilution of the seminal fluid for selection procedures or reduces the amount of dilution required.

A further object of the present invention is to provide an improved selection device and method where the same amount of medium may be used irrespectively of the volume of seminal fluid available.

A further object of the present invention is to provide an improved selection device and method wherein the exposure of the seminal fluid to oxygen before, during and/or after the selection procedure is reduced.

A further object of the present invention is to provide a selection device and method wherein wetting of the fluid connection is improved.

Furthermore, it is an object of the present invention to provide an improved selection device and method that prevents contamination of the collected sample by spermatozoa with strand breaks.

A further object of the present invention is to reduce the time required for the selection procedure.

The above-mentioned objectives are achieved by the improved selection device according to the claims. Further aspects, improvements and variations are disclosed in the Figures and the description.

In the context of the present disclosure, the terms "upper" and "lower" denominate those parts of the device located closer to the upper end and the lower end of the device, respectively, when the assembled device is held in an upright manner such that the first and second fluids can be received in the chambers.

According to an embodiment of the invention, the device for spermatozoa selection comprises a first chamber configured to receive a first, seminal fluid; a second chamber configured to receive a second fluid, the second chamber being in fluid communication with the first chamber by means of at least one duct having a first opening to the first chamber and a second opening to the second chamber; and a displacement means adapted to displace at least some of the first, seminal fluid towards or to the first opening. In preferred embodiments, the displacement means is adapted to displace the first, seminal fluid such that the upper surface, i.e., the filling level, of the first, seminal fluid is arranged at a predetermined distance from the first opening.

As the filling level of the first, seminal fluid in the first chamber may be adjusted with the displacement means, the device of the present disclosure can be used with different volumes of first, seminal fluid. The displacement means allows adapting the volume and/or the shape of the first chamber such that it may be used with seminal fluid volumes as small as 1 ml or less, preferably 0.5 ml or less. Semen samples of small volume, therefore, require less or no dilution.

In the context of the present invention, the term fluid may relate to any fluid that allows self-propelled movement of motile cells, in particular liquids or gels. Thus, each of the first and second fluids may also be denominated as liquid or gel.

The first, seminal fluid preferably is a seminal fluid which might be of poor quality, such as a seminal fluid comprising a substantial amount of spermatozoa with decreased motility and/or maturity, particularly spermatozoa with meiotic alterations, aneuploidy or sperm DNA damage, particularly sperm DNA fragmentation, e.g. DNA strand breaks. For example, the first fluid may comprise at least 15% oligo-, at least 32% astheno-, and/or at least 4% teratozoospermia based on the total amount of spermatozoa in the fluid. In embodiments, the first, seminal fluid may be a semen sample (i.e. ejaculate, in particular human ejaculate) of a patient. This ejaculate may be, for example, substantially unmixed and/or fresh ejaculate (e.g., ejaculate that has been rested for less than 20 min., 15 min. or less, 10 min. or less, or 5 min. or less and/or ejaculate that has not been mixed by repeated pippeting or other means). Hence, the sperm sample used as the first liquid may have been ejaculated less than 20 min., less than 15 min., less than 10 min., or less than 5 min. before use. The ejaculate, therefore, may comprise different phases, some of which may be highly viscid. However, the first fluid may also be a fluid with other motile cells, which may also be selected by the device of the present invention. Most preferably, the first, seminal fluid comprises a substantial amount of spermatozoa with DNA strand breaks.

The second fluid preferably is a medium for receiving spermatozoa or other motile cells, e.g., a buffer medium. Selected cells are preferably received in the second fluid contained in the second chamber during the selection process. The second fluid may then be extracted, e.g. by means of a pipette, and used in or further processed for artificial reproductive technologies (e.g., artificial insemination), cryopreservation or diagnostic purposes. Alternatively, one or several ova may be located in the second chamber. Such configuration may be used, for example, to simulate more closely a natural and physiological selection of sperm during in-vitro fertilization.

When the duct is filled with a liquid, the duct preferably provides a liquid bridge between the first chamber and the second chamber. Preferably, spermatozoa in the first chamber can move along this liquid bridge to the second chamber when the fluids in the first and second chambers reach the first and second openings of the duct, respectively.

According to the present invention, the first chamber may be provided by a vessel with a closed lower end, preferably a tubular vessel, such that the first, seminal fluid gathers at said closed lower end under the effect of gravity. The closed lower end may be of any suitable shape, for example conical, truncated, rounded (e.g., hemispherical), or flat.

Further, the lower end of the vessel may be shaped to be self-standing. For example, the lower end may be provided with a stand, which may be formed by a cylindrical protrusion projecting over the closed lower end. The vessel may also be formed to be self-standing on a flat lower end.

The vessel may further be provided with an open upper end, through which the first, seminal fluid may be brought into the first chamber, e.g., by introducing it with a pipette. The vessel may be formed of any suitable material, for example, plastics or glass. Translucent or transparent materials are preferred.

According to the present invention, the displacement means may comprise a displacement element (which may also be denominated as a displacement body) and/or a shaft for manipulating the displacement means. The displacement element preferably is located at the lower end of the displacement means. The displacement element preferably provides a solid body that may be introduced into the first chamber and that may have a volume of at least 0.5 cm$^3$, at least 1 cm$^3$, at least 2 cm$^3$, or at least 3 cm$^3$. The shaft preferably is hollow and opens out into the second chamber. The shaft and the second chamber may be fluidly connected such that the second fluid can be filled into the second chamber through the shaft and/or such that the second fluid can be collected by extending a pipette through said shaft into the second chamber, for example, once the separated spermatozoa are contained therein.

The displacement element and the shaft may be integrally formed or connected in a fixed or detachable manner. Any suitable material, for example, plastics or glass, may be used to form the displacement body and/or the shaft. Again, translucent or transparent materials are preferred.

The displacement means preferably is received within the first chamber and/or the vessel in a slidable manner, thereby ensuring safe and easy manipulation of the device. More preferably, the displacement means is concentrically received in the vessel and slidable along the vessel's longitudinal axis. Spacers and/or guides may be used to properly define the position of the displacement means and guide the displacement means within the vessel. Alternatively or additionally, the vessel and the displacement means (and/or further components connected therewith) may be provided with interacting threaded portions in order to guide the displacement means into the vessel and/or in order to maintain the displacement means at a certain position relative to the vessel during the selection procedure. For example, the shaft may be provided with an external threading and the vessel itself and/or an element attached to the vessel (e.g., a cap of the vessel) may be provided with an internal threading. In this case, the depth of the displacement means in the vessel may be defined by turning the vessel and the displacement means relative to each other, whereby the displacement means moves up or down in the vessel along the screw threading (i.e. out of or further into a first seminal fluid contained in the vessel, respectively).

The second chamber may be located in the vessel when the device is assembled. As such, the second chamber forms in use a "central" or "inner" chamber, while the first chamber forms in use a "surrounding" or "outer" chamber. In other embodiments, an outer receptacle may form the second chamber and receive a vessel forming the first chamber therein.

The second chamber may have a volume of 0.5 ml or less. In embodiments, part of this volume may be provided by the hollow shaft.

At least a part of the displacement element may have a hemispherical, substantially hemispherical, conical, substantially conical, cylindrical, or substantially cylindrical outer surface. The outer surface of the displacement means may or may not match the inner surface of the first chamber. The lower portion of the displacement means and/or the displacement element may have an outer shape that generally corresponds to the inner shape of the closed lower end of the vessel. A variable gap may be formed between the displacement means and the vessel. The gap may be formed such that it increases (e.g., in width) from a lower part of the first chamber towards an upper part of the first chamber when the displacement means is inserted as far as possible into the vessel ("fully inserted position"). For example, the outer surface of the displacement element may follow the inner surface of the first chamber along inferior sections thereof, and separate from the first chamber along upper sections, such that at least a substantial portion, preferably substantially all or most of the first, seminal fluid in the first chamber is gathered in the upper section proximate the first opening in a collection space formed between the first chamber and the displacement means. However, the displacement means may also have a flat bottom surface.

In preferred embodiments of the invention, the second chamber may be comprised in the displacement means. The second chamber may be integrally formed with the displacement means, in particular the displacement element, or connected therewith in a fixed manner. For example, the displacement element may be provided with an opening or hollow surrounded by an upwardly extending rim that forms the second chamber. This allows configuring the device in a space-saving and user-friendly manner. Moreover, the displacement element may also be provided by the second chamber itself (together with the wall surrounding it).

The displacement means can further comprise a ring-shaped cover. The ring-shaped cover may extend along or around the periphery of the rim at a defined distance, thereby forming the duct between the rim and the ring-shaped cover. The ring-shaped cover preferably is located at least 0.1 mm, preferably at least 0.2 mm, and more preferably between 0.3 mm and 0.4 mm from the rim for this purpose. Accordingly, the duct preferably has a width of at least 0.1 mm, more preferably at least 0.2 mm and most preferably between 0.3 mm and 0.4 mm. The stated distances and/or widths allow optimal filling and wetting of the duct by capillary action exerted on the first, seminal fluid and/or the second fluid. This ensures that the duct forms the liquid bridge between the first chamber and the second chamber. The ring-shaped cover may be formed integrally with or connected to the shaft in a fixed or detachable manner. The ring-shaped cover may be formed from any suitable material, for example plastics or glass. Further, the ring-shaped cover (in addition to or instead of the spacers/guides mentioned above) may help defining the position of the displacement means in the vessel, for example by maintaining the displacement means in a concentric position.

According to other embodiments, the duct may have a maximal width of 1 mm, preferably 0.5 mm along its entire length or at least a segment.

The length of the duct preferably is between 2 to 40 mm, more preferably between 5 to 35 mm, most preferably between 5 to 15 mm as measured from the first opening to the second opening, for example when considering a cross section of the device along its longitudinal axis. This ensures filling of the channel by capillary action and optimal enrichment of DNA strand break-free spermatozoa in the second chamber, whereas longer ducts may lead to an undesirable selection of spermatozoa according to sex characteristics.

The duct preferably comprises at least a first segment that extends in a direction having a directional component towards the upper end of the device and at least a second segment that extends in a direction having a directional component towards the lower end of the device. When following the duct from its first opening to its second opening, the first, upwardly extending segment preferably is prior to the second, downwardly extending segment. Preferably, the course of the duct described above can be appreciated when considering a cross section along the longitudinal axis of the device.

According to the present invention, the duct may have a U-, V-, or W-shaped cross section, for example, when considering a cross section along a longitudinal axis of the device and/or a longitudinal axis of the displacement means. This means that the duct may have the shape of a U, a V, or a W when a cross section of the device and/or the displacement means along the respective longitudinal axis is considered. In embodiments, the duct may be substantially U-, V-, or W-shaped.

The duct preferably extends along a part, most or the entire perimeter of the second chamber. The selection device may comprise several such ducts extending along the perimeter of the second chamber according to embodiments of the invention.

The cross section preferably has the shape of an inverted U, a first leg of the U extending into the first chamber and a second leg of the U extending into the second chamber. The duct may, thus, provide a fluid communication between said first chamber and said second chamber that requires motile cells (e.g., spermatozoa) located in the first chamber to "swim" or move against gravity along at least a segment of the duct in order to arrive at the second chamber.

Preferably, the second leg of the U is longer than the first leg, i.e., the second leg extends further into the second chamber than the first leg extends into the first chamber. In other embodiments the first leg may be longer than the second.

According to the present invention, the device may be provided with a scale for assessing a volume of the first, seminal fluid in the first chamber (first scale). Said first scale may be provided, for example, on the vessel forming the first chamber, e.g., on an inner or an outer surface thereof. Additionally or alternatively the volume introduced into the first chamber may also be assessed by other means, for example a pipette.

A scale for assessing travel of the displacement means may also be provided (while the term "second scale" is used below, it will be clear to the skilled reader that this scale may also be provided independently of the "first scale" mentioned above). The second scale may be used for assessing how far the displacement means and/or the displacement element has been introduced into the first chamber. The scale may be provided, for example, on the displacement means or the vessel forming the first chamber, whereas the other of the displacement means and the vessel may be provided with a reference line or indentation for measuring travel on the second scale. Marks, lines, indentations and/or similar means may form the gradations of the first and/or second scales. The gradations may be spaced apart in a regular or irregular manner.

According to embodiments of the invention, the second scale may indicate the travel required for the displacement means dependant upon the volume of first, seminal fluid provided in the first chamber. This means, the second scale may indicate the optimal position of the displacement means and/or the displacement element dependant upon said volume of first, seminal fluid. The gradations of the second scale may indicate how far the displacement means should be introduced into the first chamber or vessel in order to displace a predetermined volume of the first, seminal fluid towards the first opening. Preferably, the second scale indicates how far the displacement means should be introduced into the first chamber or vessel in order to displace the first, seminal fluid such that a fixed gap remains between the first, seminal fluid and the first opening, regardless of the volume of first, seminal fluid provided in the first chamber.

In embodiments of the invention, the gradations of the second scale may be provided by corresponding colour-codes on the displacement means and the vessel. These colour-codes may comprise fields or gradations of different colours provided such that the depth of the displacement means in the vessel is adequate for the volume contained in the first chamber when the a certain colour of one code overlaps with the same or a corresponding colour of the other code. Also the first scale may be formed as a colour-code, in which case the first scale may form the colour code on the vessel required for the second scale.

The extent to which the fluid level in the first chamber raises when the displacement means is inserted depends on several factors, including the shape of the first chamber and the shape of the displacement means. It may not be linearly related to the travel of the displacement means. While a large travel may be required for small volumes, the difference in travel may be minimal for larger volumes. The second scale may account for these effects. For example, the second scale may be non-linear and the distance between adjacent gradations may diminish with increasing volume. The second scale may be used to insert the displacement means to the required travel after determining the volume of first, seminal fluid in the first chamber with the first scale and/or other means (e.g., a pipette).

In mechanical or electromechanical implementations of the invention, the travel of the displacement means may be measured with sensors and/or controlled by actors.

In embodiments, the present invention may also include a closure means for sealing the first chamber relative to the environment, e.g., by covering and/or sealing the open upper end of the vessel. The closure means may be configured for sealing the first chamber (which may be an outer or surrounding chamber, as described above) in an airtight manner.

The closure means may be a plug, for example, a plug with a through hole that can be connected to the shaft. The closure means may be formed of any material suitable for sealing the first chamber in an airtight or substantially airtight manner (e.g., rubber or other polymeric materials, such as thermoplastic materials). When the first chamber is sealed relative to the environment, the fluid in the first chamber will not be drawn into the second chamber even when collecting the fluid contained therein, for example, with a pipette. Therefore, the plug avoids that spermatozoa with strand breaks are drawn into the second chamber when DNA strand break-free spermatozoa contained therein are collected.

In embodiments, a cap (e.g., a screw cap that can be screwed onto the vessel or a cap with a bayonet fit) may be used for covering and/or closing the vessel. The cap may have an attachment structure (e.g., a threaded portion with an internal or external thread, a bayonet fit, or a snap fit) that engages or is engaged by an attachment means (e.g., an external or internal thread, attachment means for a bayonet fit, or a snap fit) provided on the vessel. As mentioned above, such cap may also function as a centering element for the displacement means and may comprise a central through-hole for the shaft in this context. Moreover, this central through-hole or another portion of the cap may be provided with an internal (or female) threading that interacts with an external (or male) threading of the shaft to define the travel of the displacement means in the vessel. The bayonet fit or screw threading used for attaching the cap to the vessel may be configured to close in the direction in which the displacement means is rotated when it is screwed into (i.e. down) the vessel in order to avoid accidental opening of the cap. As such, the shaft may be provided with a left-hand thread when the bayonet fit closes to in the clockwise direction and vice-versa.

According to other embodiments of the invention, the cap may be provided with one or several vent holes. In this context, the plug may be used to selectively close these vent holes. For example, the plug may be attached to the cap in a rotatable manner such that it can be rotated from a first position, in which the vent holes are open, to a second position, in which the vent holes are closed and, preferably, sealed in an airtight manner. The plug may be provided above the cap for this purpose. According to other embodiments of the invention, the cap may be used for pressing the plug against the vessel in order to provide an airtight seal.

The plug may be separate from the cap, attached thereto or formed integrally therewith.

The closure means (e.g., the plug) may be inserted into the first chamber after sealing it therewith. More specifically, the closure means may be inserted into the vessel after sealing it, for example, at its open upper end. While any suitable type of closure means may be employed for this purpose, the closure means may be configured such that they can be inserted a predetermined and/or fixed depth into the vessel. For example, the plug may comprise an abutment surface that inhibits insertion of the plug when the predetermined depth is reached. Optionally, the cap may be used for inserting the plug (with or without an abutment surface) to the predetermined depth. Insertion of the closure means into the vessel may lead to a positive pressure in the first chamber, which may cause some of the fluid in the duct (e.g., fluid in the inner part of the duct proximate the second opening) to flow into the second chamber. This may increase spermatozoa yield obtained by the selection procedure.

According to the present invention, the device may further comprise a pipette containing a predetermined volume of the second fluid. This ensures that the correct volume of the second fluid is used and that the duct is wetted in an optimal manner. Since the level of the first, seminal fluid in the first chamber may be adapted with the displacement means, the volume of second fluid in the pipette may be fixed and may be independent of the volume to be provided in the first chamber. This may ensure that a correct volume of second fluid is provided in the second chamber and reproducible results are obtained. The pipette may be configured and adapted for injecting the second fluid into the second chamber of the device and/or extracting fluids from said second chamber. Optionally, the pipette may be configured such that the fluid is not injected into the second chamber too quickly. This may be useful for preventing formation of air bubbles in the second fluid, which might occlude part of the duct. Also, the pipette may be configured such that the fluid is not injected into the second chamber too slowly. This may be useful for ensuring that the duct is filled adequately. In embodiments, the volume of second fluid provided in the pipette may be 0.5 ml or less, corresponding to the amount which ideally is injected into the uterus.

The selecting device of the present invention may be reusable or disposable, i.e., intended for single use. Disposable use may be preferred in accordance with regulatory provisions.

The present invention may also relate to a kit comprising a device for selecting spermatozoa and a pipette containing a predetermined volume of the second fluid.

Further, the present invention may relate to a method for selection of motile cells (e.g. spermatozoa) by using the device described above. The method may include the steps of (a) providing a first fluid comprising motile cells in the first chamber of the device; (b) providing a buffer medium in the second chamber of the device; (c) connecting the first chamber and the second chamber by means of a liquid connection; and (d) displacing at least some of the first fluid towards, proximate the first opening of the duct with the displacement means.

As discovered by the inventor, this method may be used to select spermatozoa for motility and/or maturity, and in particular to obtain a fluid in the second chamber enriched with DNA strand break free spermatozoa.

As further discovered by the inventor, the above method leads to substantially higher yields of mobile cells (in particular spermatozoa) in the second chamber when the first fluid is fresh and/or untreated ejaculate, i.e., ejaculate that has not been liquefied by a resting period and/or pippeting. Therefore, fresh and/or substantially untreated ejaculate is preferably used as the first fluid. The ejaculate may be used directly after ejaculation. The patient may ejaculate directly into the vessel of the selection device according to the invention or into a funnel structure attached thereto (e.g., the funnel structure of the present invention). Directly thereafter (i.e., for example, without a waiting period or a waiting period of less than 20 min., 15 min. or less, 10 min. or less, or 5 min. or less), separation may be started, e.g., by introducing the displacement means into the first chamber provided by the vessel.

According to a further embodiment of the invention, the seminal plasma remaining after spermatozoa selection may be used in other procedures, for example, seminal plasma infusion.

According to a further aspect, the present invention relates to a funnel structure for filling a liquid into a vessel. The funnel structure preferably has an inlet opening having a first cross-sectional area and an outlet opening having a second cross-sectional area, the first cross-sectional area being larger than the second cross-sectional area. The inlet opening preferably is positioned such that it is above the outlet opening when the funnel is in an upright position. Further, the funnel structure preferably comprises an intermediate opening. When the funnel structure is in an upright position, said intermediate opening preferably is disposed between the inlet opening and the outlet opening.

The funnel structure preferably is configured for being attached to a vessel and may comprise an attachment structure. Suitable attachment structures may include, inter alia, a portion of the funnel structure providing a form fit and/or a friction fit with the vessel. For example, the funnel structure may be provided with a portion having an internal thread, an external thread, a bayonet fit, a snap fit and/or a screw on collar. The attachment structure preferably is configured to provide a leak-proof attachment with the vessel, such that a liquid contained in the vessel cannot leak in the area of the attachment, for example, when the vessel and the funnel structure are laid horizontally or turned upside-down. Preferably, the funnel structure is provided with a cylindrical portion (e.g., a cylindrical portion with an internal thread) that surrounds an opening of the vessel and, therefore, also prevents the vessel's inner walls from being contacted by foreign elements. Thus, the likelihood of contamination is minimized.

The funnel structure preferably has a recuperation compartment or chamber that is configured to collect and retain at least part of the liquid contained in the vessel when the vessel and/or funnel is laid horizontally or turned upside-down, for example, when it is knocked over inadvertently. The recuperation compartment preferably is further configured such that the liquid collected and retained therein flows back into the vessel when the vessel is positioned in an upright position thereafter. The recuperation compartment may have an upper closed end and be open in a downward direction. The opening of the recuperation compartment may be provided around the intermediate opening.

The funnel structure preferably comprises a first circumferential wall that tapers inwardly when following the longitudinal axis of the funnel structure in a direction from the inlet opening to the outlet opening. The first circumferential wall preferably has a generally conical shape along at least a segment thereof. The first circumferential wall may form a first funnel, which may be an outer funnel according to aspects of the invention. The first circumferential wall may extend to and/or form the outlet opening. Furthermore, the first circumferential wall may extend proximate the inlet opening.

The funnel structure preferably also comprises a second circumferential wall. The second circumferential wall may taper inwardly when following the longitudinal axis of the funnel structure in a direction from the inlet opening to the outlet opening and may have a generally conical shape along at least a segment thereof. The second circumferential wall may extend generally parallel to the first circumferential wall along at least a segment. Further, the second circumferential wall may form a second funnel, which may be an inner funnel that is disposed within the outer funnel entirely or along a segment. The first circumferential wall may extend to and/or form the inlet opening. Furthermore, the first circumferential wall may extend to and/or form the intermediate opening.

The recuperation compartment may be provided between the first and second circumferential walls. The first and second circumferential walls preferably are connected by an upper wall, which may form the upper closed end of the recuperation chamber according to aspects of the disclosure. While the term "circumferential" is used, it should be noted that neither the funnel structure nor the first and second circumferential walls have to be rotationally symmetric. In embodiments, one or both of these walls may or may not surround the funnel structure entirely.

The first and second circumferential walls of the funnel may be formed integrally, for example, from a single material (e.g., a polymeric material or glass).

The funnel structure may comprise an air vent. The air vent preferably provides an additional fluid connection between the interior of the vessel to which the funnel structure is attached and the environment. Thus, formation of air bubbles may be prevented when the funnel structure is filled. The air vent preferably provides a fluid connection between the interior of the vessel and the recuperation compartment. In this case, any liquid flowing out of the vessel through the air vent may be collected in said recuperation compartment. The air vent may be provided by a hole traversing the first circumferential wall.

The funnel structure may be reusable but, preferably, is a disposable article configured for single use. The funnel structure may be particularly advantageous for laboratory applications.

The funnel structure provides an improved type of funnel that prevents liquids, for example valuable liquids, from being spilled when the vessel into which the liquids are filled is knocked over or turned around. Advantageously, the liquid is received in the recuperation compartment and, subsequently, can be filled back into the vessel without having contacted the environment. Therefore, contamination of the liquid and/or the environment can be prevented. In addition to liquids, the funnel structure may also be used with other substances that are filled into some kind of receiving structure by means of a funnel Other substances may include powders and/or grains.

The funnel structure and the selection device of the present invention may be adapted for combined use. For example, any of the devices described above may comprise an attachment means configured to attach the device, for example its vessel, to the funnel structure (e.g., by means of the attachment structure). The attachment means may comprise, inter alia, a portion having an internal thread, an external thread, a snap fit, a bayonet fit and/or a screw on collar. The attachment means may be provided proximate the open upper end of the vessel. A kit comprising the funnel structure and a selection device may be provided according to aspects of the present invention. It should be noted, however, that the funnel structure may also be provided separately.

According to a further aspect, a stand for a vessel is provided. The stand may be used for holding the device of the present invention in an upright position, e.g., when the funnel structure is attached to the device and/or when the selection procedure is performed. A kit comprising a stand, a funnel structure and/or a selection device may be provided according to aspects of the present invention.

The funnel structure described above is particularly advantageous for collecting sperm samples. Male patients that have to provide such samples are often nervous and, sometimes, knock over the vessel in which the sample is received. The funnel structure prevents loss of all or most of the sample in this case. It is also particularly useful in this context that the funnel structure may prevent contamination of the inside of the vessel. For example, the funnel structure may prevent the patient from contacting the inner surfaces of the vessel with the hands or the penis, thereby reducing the likelihood of contamination.

Moreover, when the funnel structure is used with the vessel of the selection device, the sperm sample may be received in the vessel used for spermatozoa selection directly. Transfers from one vessel to another, which might lead to mechanical and/or chemical damage of the sperm cells and loss of the sperm cells remaining in the used vessels, are thus avoided.

The Figures described below disclose embodiments of the invention for illustrational purposes only. In particular, the disclosure provided by the Figures is not meant to limit the scope of protection conferred by the invention. The Figures are schematic drawings only and embodiments shown may be modified in many ways within the scope of the claims.

FIG. 1: Sectional view of a prior art selection device disclosed in WO 03/031594.

FIG. 2: Exploded view of the prior art selection device shown in FIG. 1.

Figures 3A, 3B:
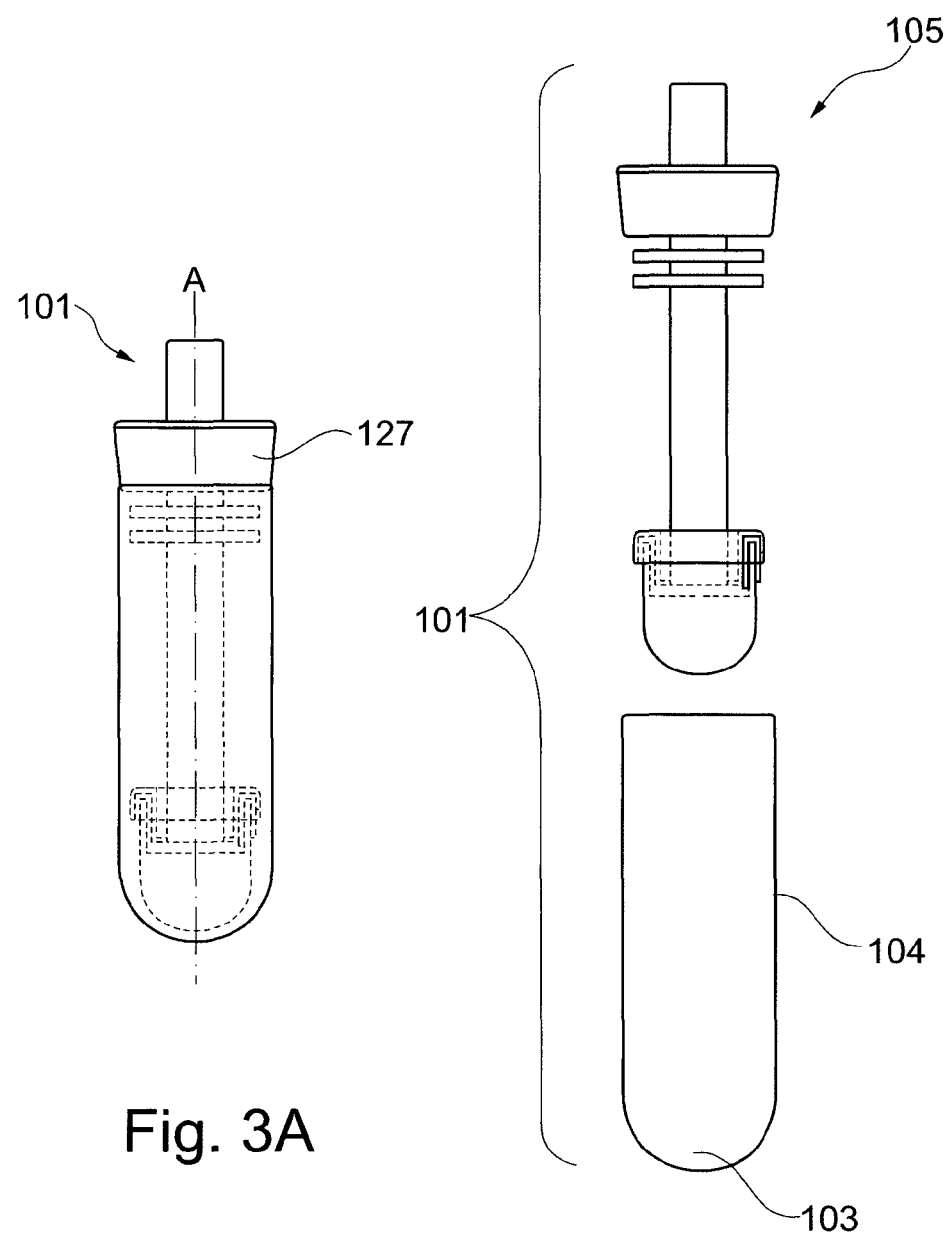

FIG. 3A: Plan view of a device for spermatozoa selection according to an embodiment of the present invention.

FIG. 3B: Exploded view of the device shown in FIG. 3A.

Figure 4:
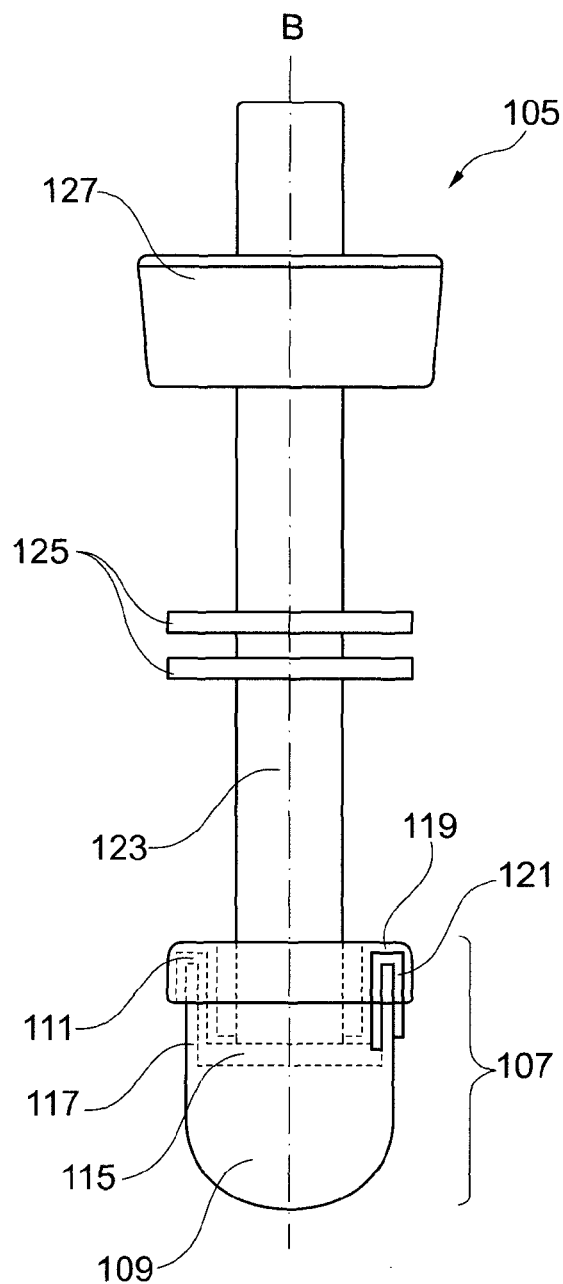

FIG. 4: Plan view of the displacement means of the device shown in FIGS. 3A and 3B.

Figure 5:
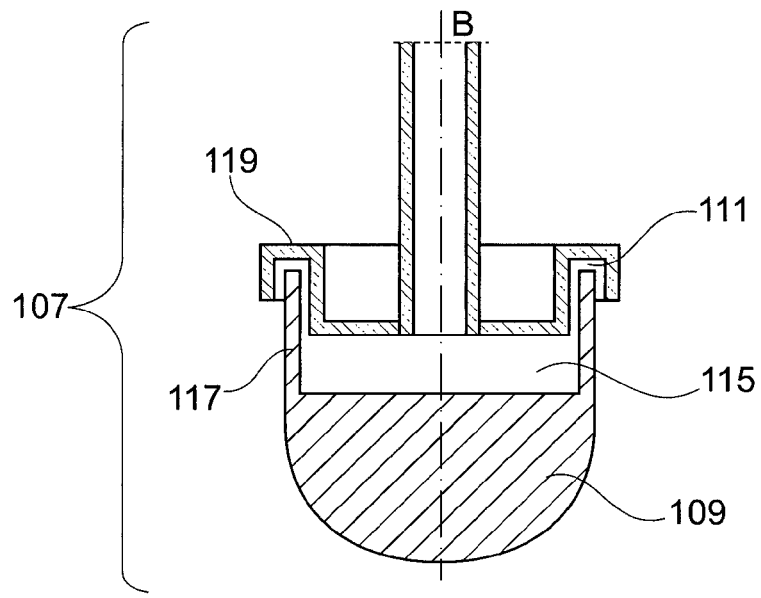

FIG. 5: Enlarged sectional view illustrating the lower portion of the displacement means shown in FIG. 4.

Figure 6:
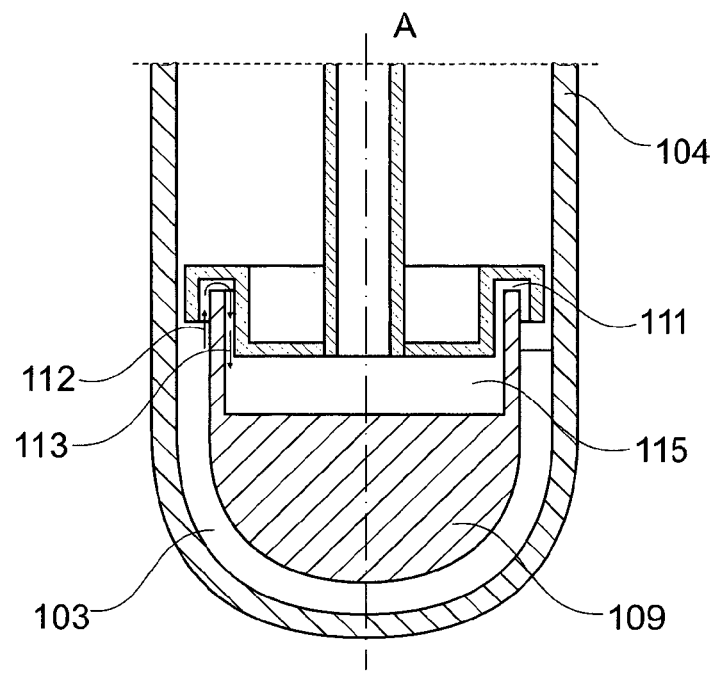

FIG. 6: Enlarged sectional drawing of the lower portion of the device shown in FIGS. 3A and 3B.

FIGS. 7A-7C: Sequence of schematic sectional drawings showing the usage of a device according to the present invention.

FIG. 7D: Schematic drawing illustrating spermatozoa selection.

FIG. 8A-8E: Sectional drawings showing the lower portion of a selection device according to various embodiments of invention.

Figures 9, 10:
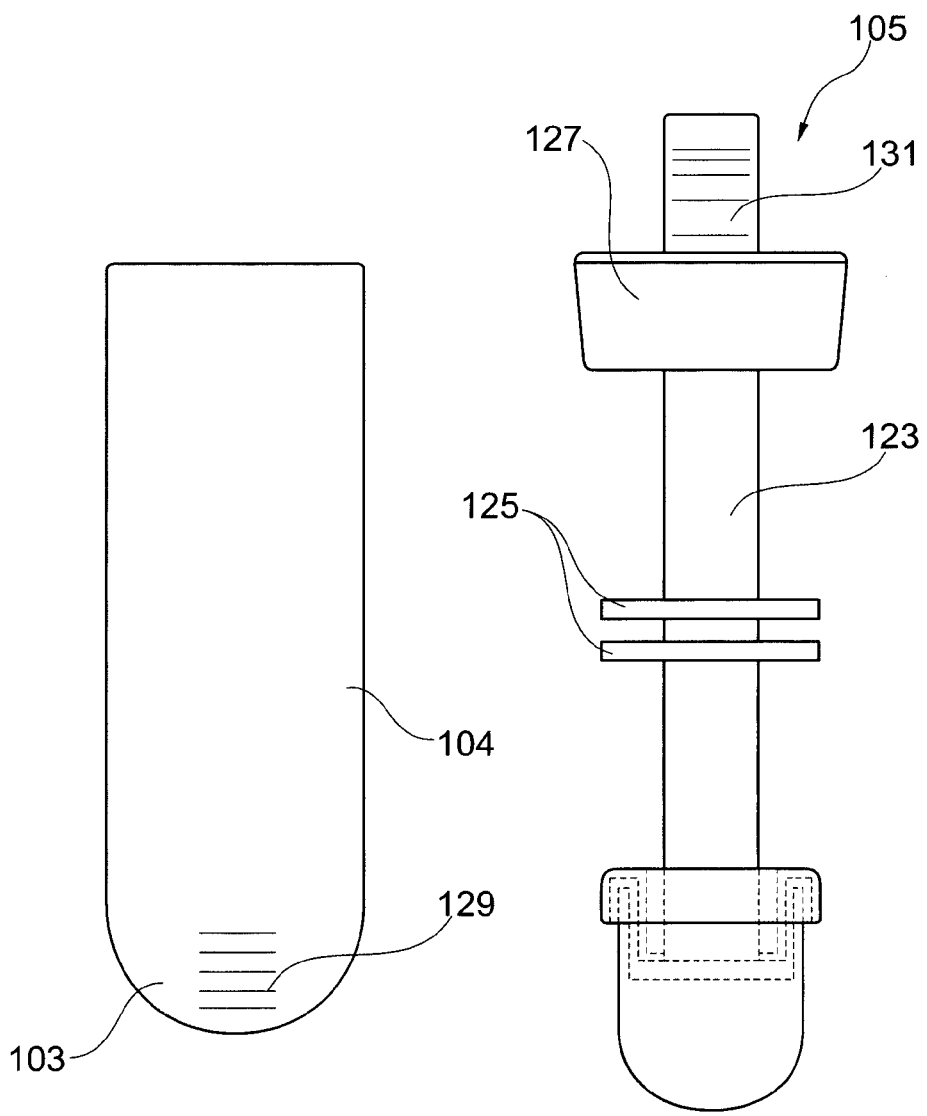

FIG. 9: Plan view showing a vessel for selection devices according to embodiments of the present invention, the vessel being provided with first and second scales.

FIG. 10: Plan view showing a displacement means for selection devices according to embodiments of the present invention, the displacement means being provided with a scale.

Figures 11A, 11B:
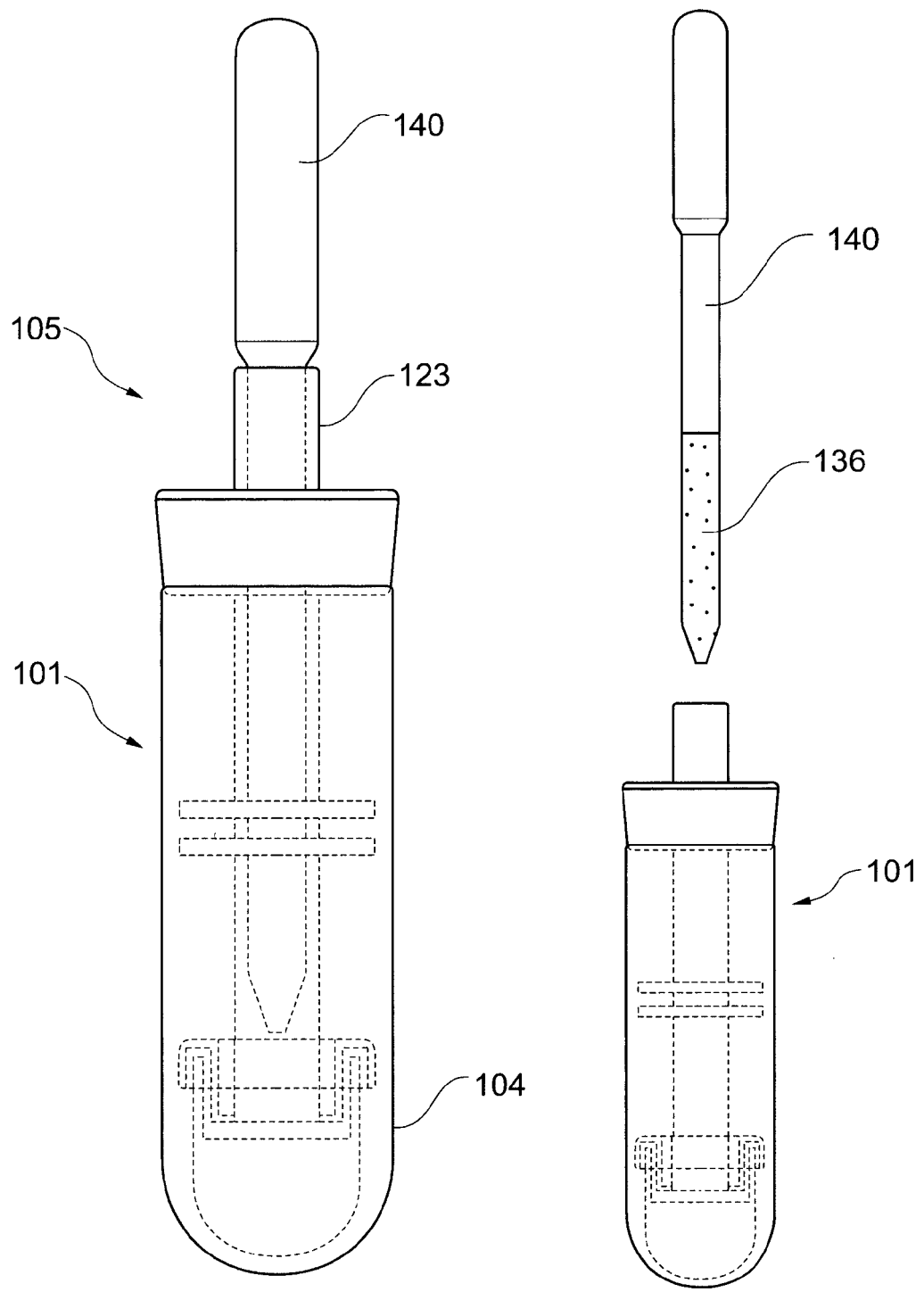

FIG. 11A: Plan view showing a kit according to embodiments of the present invention.

FIG. 11B: Exploded view of the kit shown in FIG. 11A.

Figure 12A:
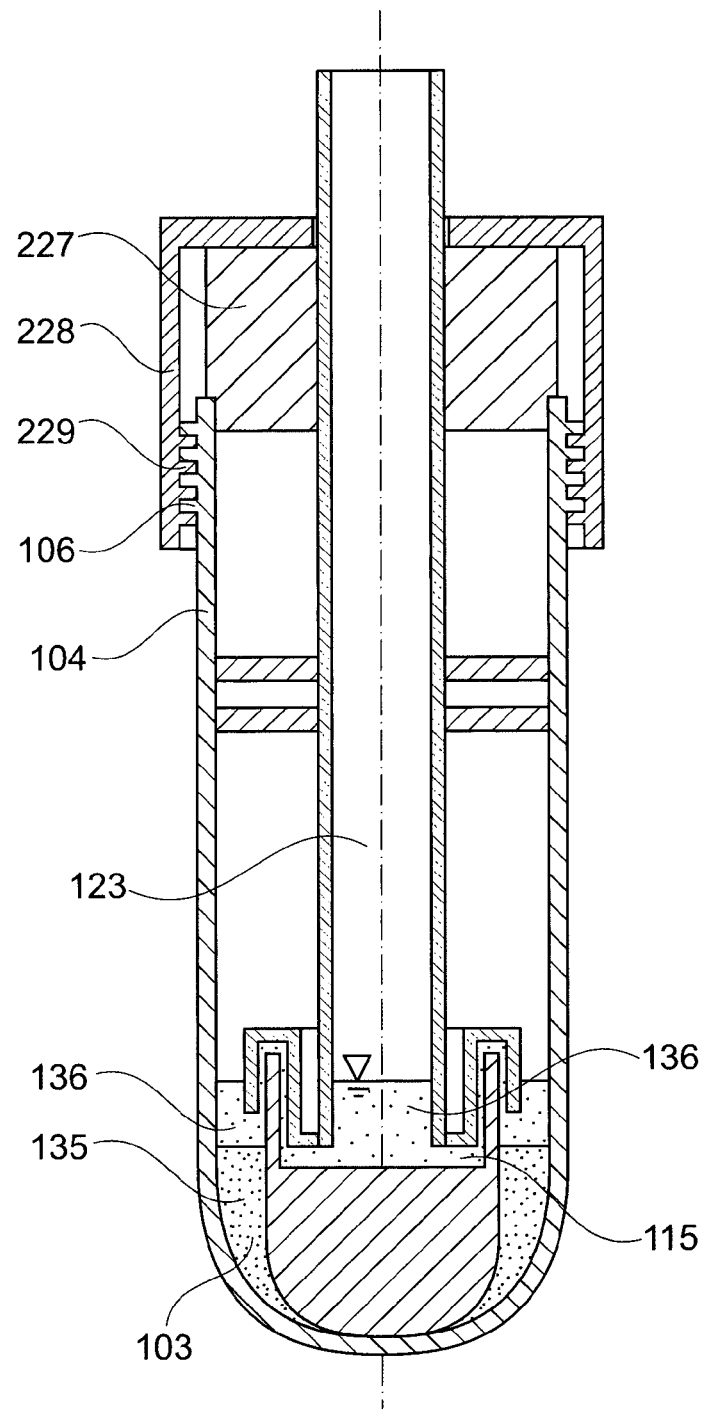

FIG. 12A: Sectional drawing of the selection device according to another embodiment of the invention.

Figure 12B:
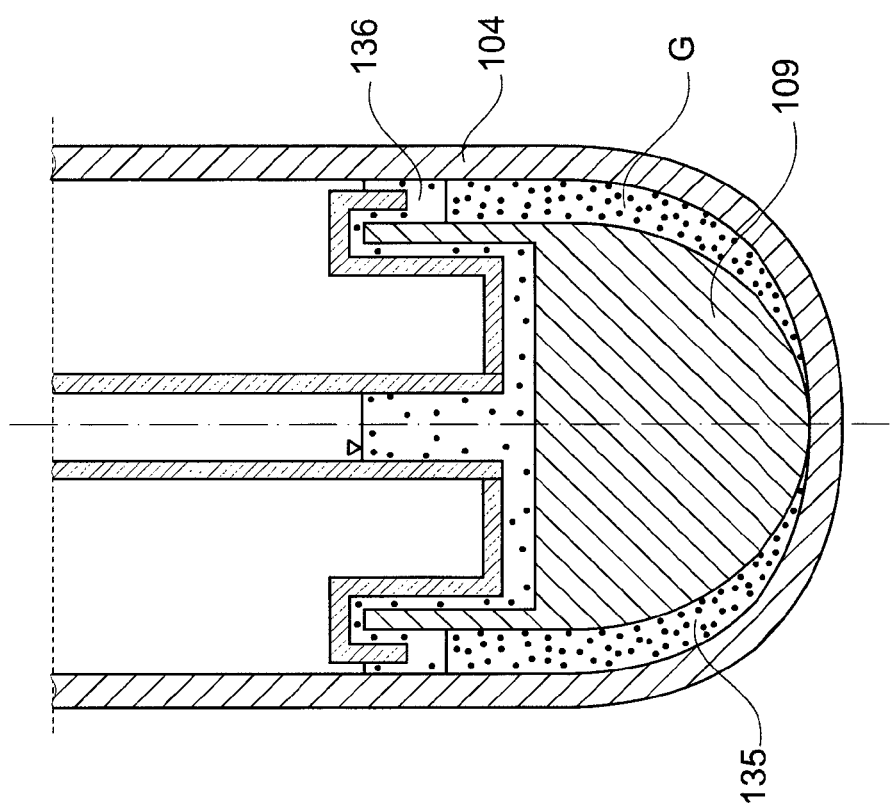

FIG. 12B: Sectional drawing showing an enlarged view of the lower portion of the selection device of FIG. 12A.

FIG. 13A: Plan view of a device for spermatozoa selection according to another embodiment of the present invention with the displacement means fully introduced into the vessel.

FIG. 13B: Section I-I of FIG. 13A.

FIG. 13C: Perspective view of the device for spermatozoa selection according to FIGS. 13A and 13B.

Figure 13D:
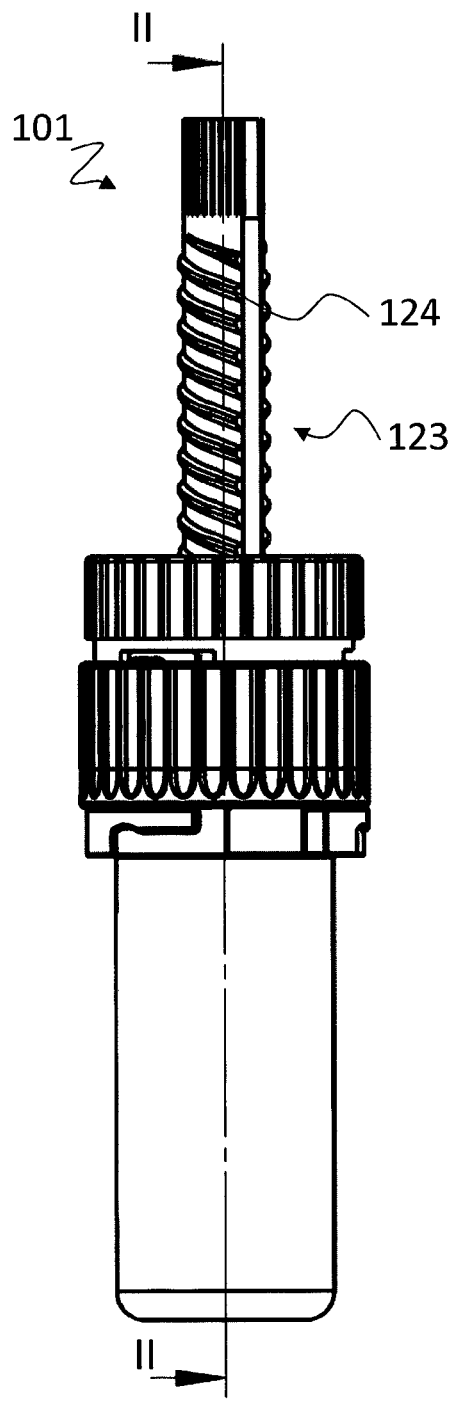

FIG. 13D: Plan view of a device for spermatozoa selection according to FIG. 13A with the displacement means at an upper end of the vessel.

Figure 13E:
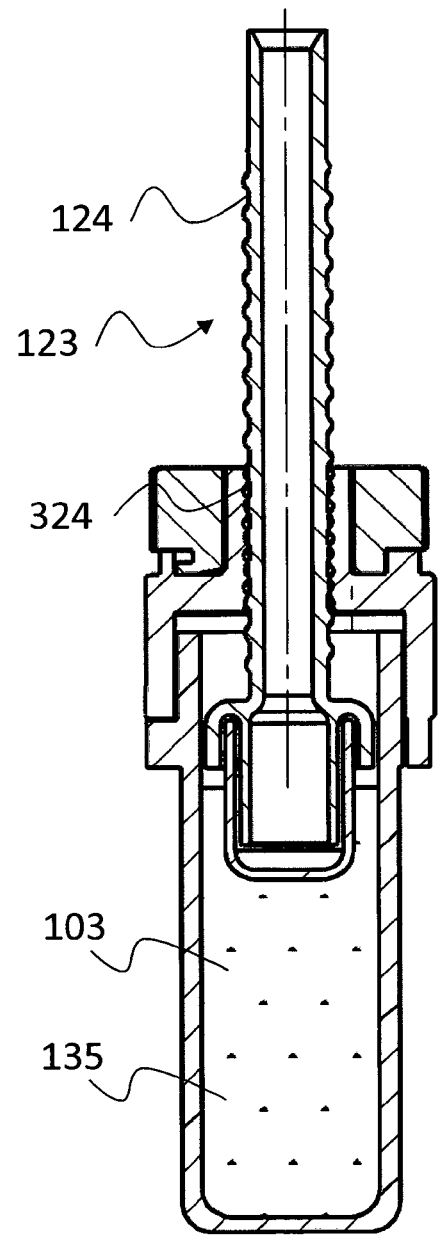

FIG. 13E: Section II-II of FIG. 13D.

Figure 14A:
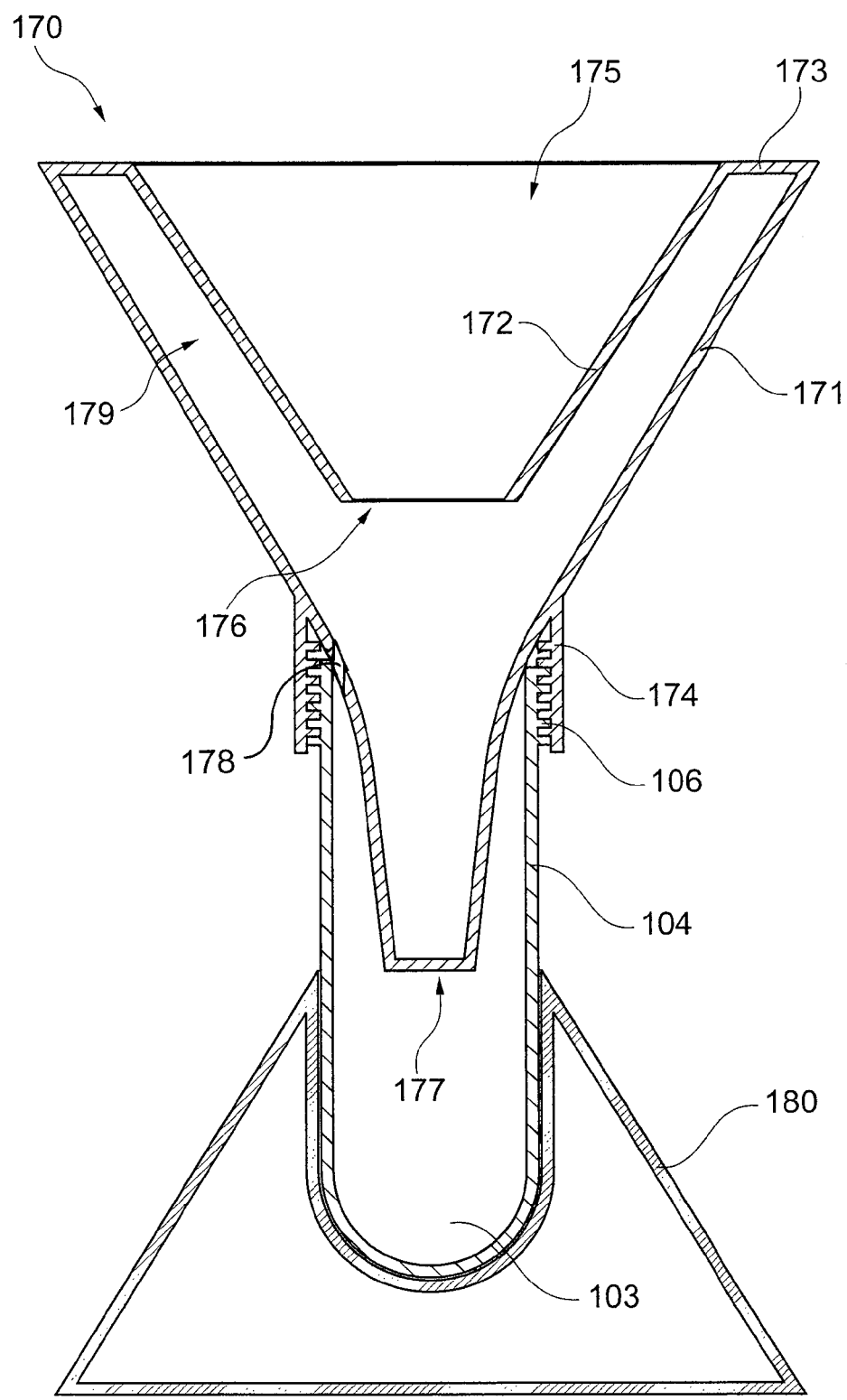

FIG. 14A: Sectional drawing showing a funnel structure according to aspects of the invention.

Figure 14B:
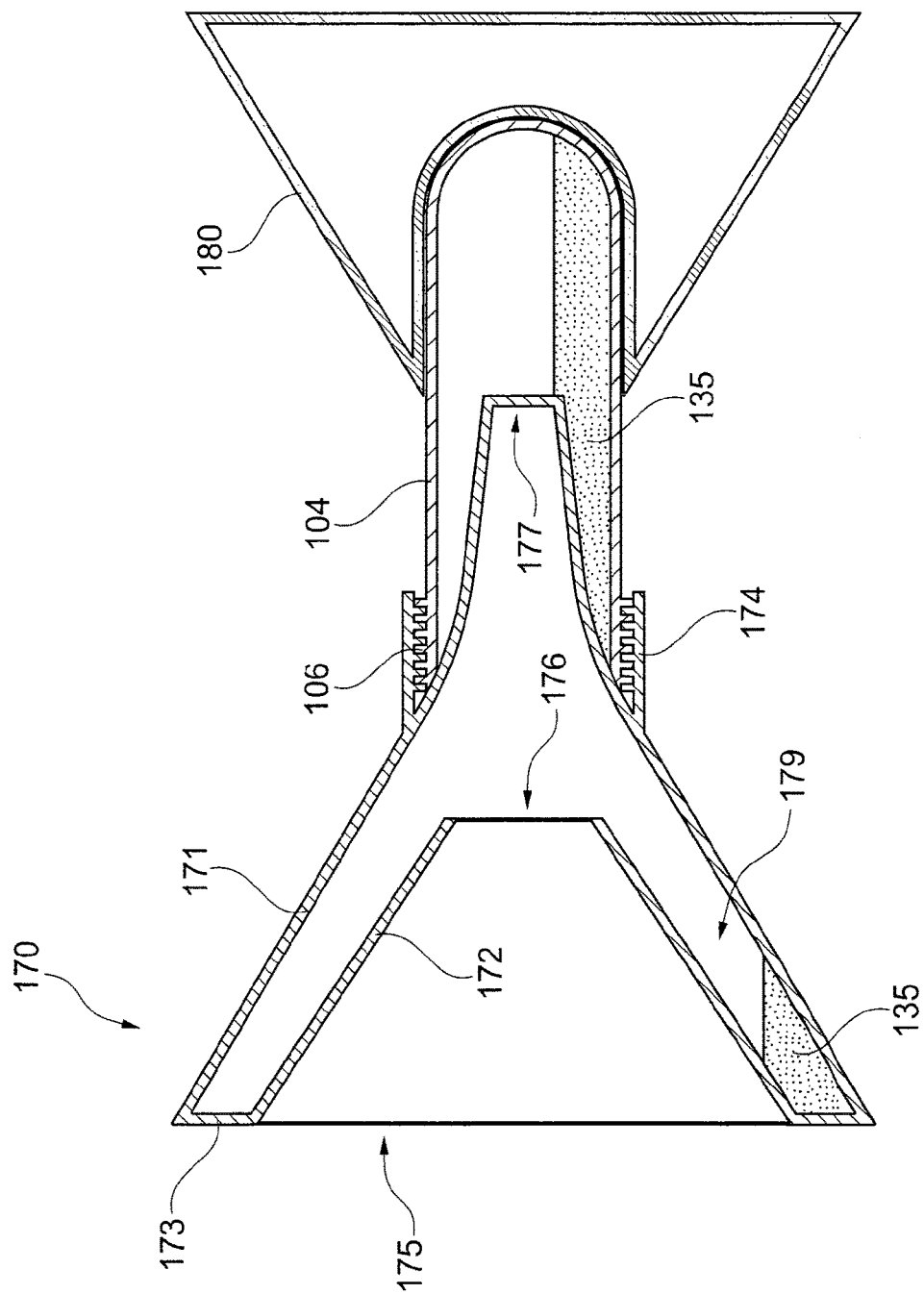

FIG. 14B: Sectional drawing showing the functional principle of the funnel structure illustrated in FIG. 13A.

Figures 15A, 15B:
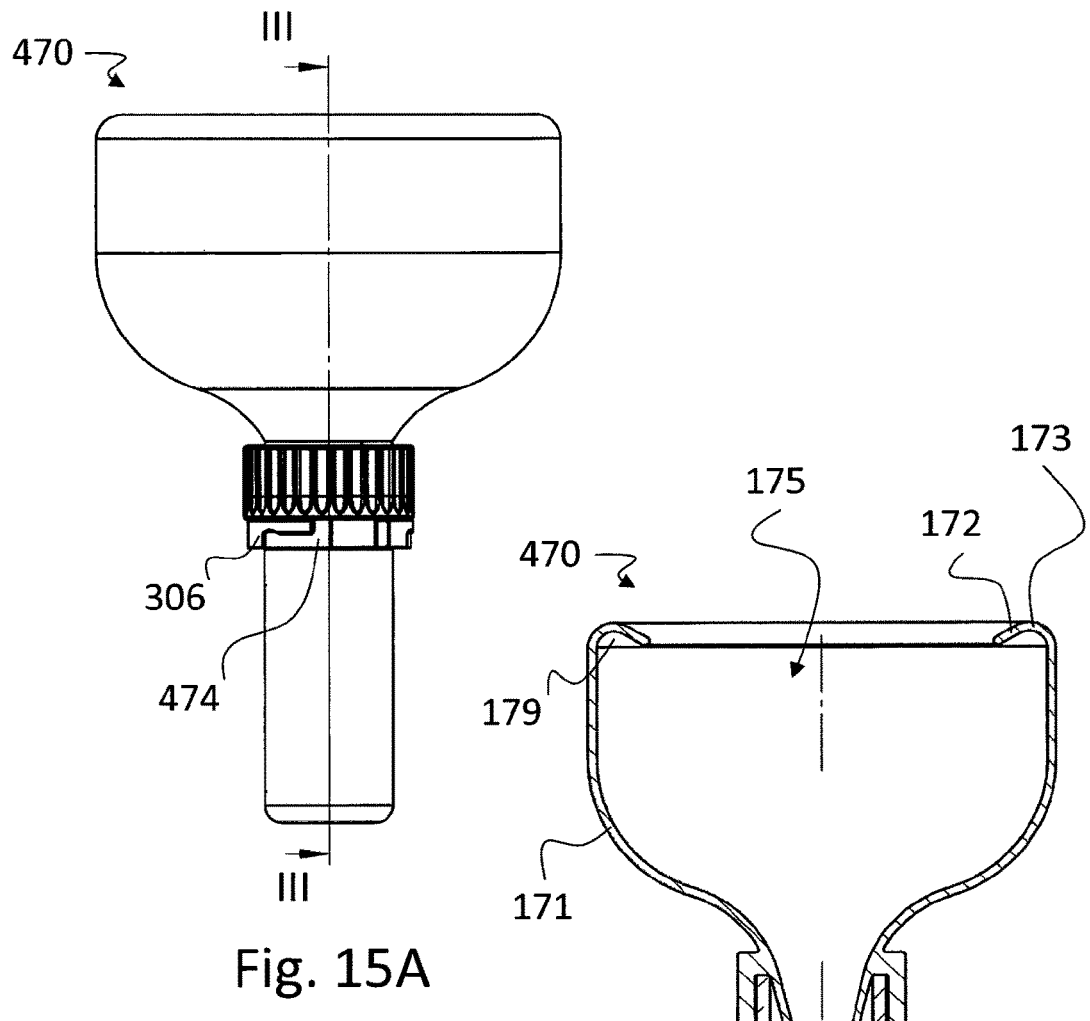

FIG. 15A: Plan view showing a funnel structure incorporating further aspects of the invention.

FIG. 15B: Section III-III of FIG. 15A.

FIG. 16: Table comparing spermatozoa concentrations achieved when using fresh, untreated ejaculate and ejaculate that rested for 15 to 30 min.

FIG. 3A shows a plane view of a device 101 for spermatozoa selection according to embodiments of the present invention. As shown, the device may be rotationally symmetric with respect to its longitudinal axis A.

As shown in the exploded view illustrated in FIG. 3B, the device 101 comprises a first chamber 103 and a displacement means 105. The first chamber 103 may be formed by an interior portion of a lower end of a vessel 104, which preferably surrounds the displacement means 105 when the device 101 is in an assembled state (see FIG. 3A). While the vessel 104 is shown with a hemispherical lower end, it is noted that the lower end of the vessel may have any suitable shape. As such, the vessel may have a conical, generally conical, truncated, rounded or flat lower end. Furthermore, the lower end of the vessel may be formed such that the vessel is self-standing.

FIG. 4 shows a plan view of the displacement means 105 illustrated in FIGS. 3A and 3B. As shown, the displacement means 105 may comprise a displacement element 109 located at a lower portion 107 thereof. The lower portion 107 may further be provided with a second chamber 115, which is provided above the displacement element 109 in the illustrated embodiment and formed integrally therewith.

The displacement means 105 may further comprise a shaft 123 for manipulating and holding the displacement means. As such, the shaft 123 may be used by a user to slide the displacement means into the vessel 104 and the first chamber 103 (see FIG. 3A). When a hollow shaft 123 as shown in the Figures is used, the atmosphere can be fluidly connected with the second chamber 115 such that the second fluid may be filled into and/or extracted from the second chamber through the shaft 123. The shaft can be provided with one or several spacers 125 in order to center the displacement means 105 in the vessel 104. The spacers ensure that the displacement means 105 is received in the vessel 104 in a coaxial manner. It should be noted, however, that also other elements connected to the vessel and/or the displacement means, for example the ring-shaped cover 119, may be used for this purpose.

As further shown, for example, in FIG. 3A, a plug 127 may be used to close the vessel 104. The plug 127 may be part of the displacement means and can be attached thereto in a fixed or slidable manner. Alternatively, the plug 127 may be formed integrally with the displacement means 105, for example, as part of the shaft 123. The plug may close the vessel 104 in a sealing, for example airtight, manner.

The details of the lower portion 107 of the displacement means are schematically illustrated in the enlarged view of FIG. 5. As shown, the second chamber 115 may be surrounded by a rim 117 having an upper end surface, an outer wall surface and an inner wall surface. A ring-shaped cover 119 may extend around at least part of the outer wall surface, the upper end surface and the inner wall surface of the rim 117 at a predetermined distance, forming a duct 111. The displacement element 109 and the second chamber 115 are integrally formed in the shown embodiment. Any suitable material may be used, for example plastic or glass.

Distance piece 121 allows maintaining the ring-shaped member 119 at the predetermined distance in order to provide the duct 111 with a predetermined width. The ring-shaped cover may be formed integrally with or connected to the shaft and may be formed of any suitable material, for example plastics or glass. The shaft with the ring-shaped cover may be connected to the displacement element in a fixed manner.

FIG. 6 schematically illustrates a cross section of the device along its longitudinal axis A. As shown therein, the duct 111 substantially has the shape of an inverted U, a first leg extending to the first chamber and a second leg extending to the second chamber. The duct 111 has a first opening 112 to the first chamber 103 and a second opening 113 to the second chamber 115. The openings 112, 113 are preferably ring-shaped. As illustrated, the U-shaped duct 111 may extend further into the second chamber 115 than into the first chamber 103. The arrows shown in FIG. 6 adumbrate the path along which spermatozoa may travel from the first chamber 103 to the second chamber 115.

Usage of the device for spermatozoa selection according to embodiments of the present invention is further illustrated by the schematic drawings of FIGS. 7A-7C. As shown in FIG. 7A, the first, seminal fluid 135 may be received in the first chamber 103 formed at the lower end of the vessel 104. Since the first, seminal fluid may be, for example, semen of a patient, the provided volume may vary considerably.

Once the first, seminal fluid 135 is received in the first chamber 103, the displacement means 105, in particular the displacement element 109, may be introduced into said first chamber 103 until the first, seminal fluid 135 is located proximate the first opening 112. In the illustrated example, the displacement means is inserted by a distance L into the first, seminal fluid. The upper surface of the first, seminal fluid, as a consequence, is displaced a distance D towards the first opening 112 (see FIG. 7B). In the illustrated embodiment, the first, seminal fluid 135 does not reach the first opening 112 entirely. Rather, a space S remains between the first, seminal fluid 135 and the first opening 112, which is subsequently covered by second fluid 136 flowing through the duct 111 when the second chamber 115 is filled. This prevents the first, seminal fluid from being drawn into the duct 111 by capillary action and, therefore, avoids that spermatozoa reach the second chamber 115 without passing the selection process. However, displacing the first, seminal fluid 135 to contact the first opening 112 may be considered for some applications. With the selection device of the present invention, the space S between the first, seminal fluid 135 and the first opening 112 may be equalized for a broad range of volumes of first, seminal fluid provided in the first chamber 135 by inserting the displacement element 109 to the appropriate depth L. Since, the volume of second fluid 136 can be kept constant and reproducible results can be obtained.

As shown in FIG. 7C, the second fluid, for example, a buffer medium is subsequently provided in the second chamber 115. As mentioned above, the second fluid preferably is drawn into the duct 111 by capillary action and/or due to the pressure exerted when filling it into the second chamber, for example, along the shaft 123 by means of a pipette. Accordingly, the duct 111 establishes a liquid bridge between the first chamber 103 and the second chamber 115, allowing spermatozoa to move along the path indicated by the arrows shown on FIGS. 6 and 7C. As schematically illustrated in FIG. 7D, spermatozoa or other motile cells in the first fluid 135 will swim or flow from the first chamber through the duct 119 into second fluid 136 contained in the second chamber.

Once spermatozoa are separated (e.g., after waiting for 15-120 min.) the second fluid may be withdrawn from the second chamber, for example, by means of a pipette introduced through the shaft 123. The first chamber 103 may be sealed relative to the environment (e.g. by closing the open upper end of the vessel 104 with the plug 127, as shown in FIG. 3A) in order to prevent first, seminal fluid 135 from being drawn into the second chamber 115 when collecting the fluid contained therein.

As will be appreciated by those skilled in the art, the sequence of the steps described above may be changed in embodiments of the invention. For example, the second fluid 136 may be received in the second chamber 115 before the displacement means is introduced into the first chamber 103. Furthermore, the displacement means may be introduced into the first chamber before the first, seminal fluid 135 is received therein.

The ring-shaped cover 119 preferably is located at least 0.1 mm, preferably at least 0.2 mm, and more preferably between 0.3 and 0.4 mm from the rim. Accordingly, the duct 111 preferably has a width of at least 0.1 mm, more preferably at least 0.2 mm and most preferably between 0.3 and 0.4 mm. As will be understood by the skilled person, the optimal widths will depend on the materials and the fluids employed, as both may influence capillary action. The length of the duct 111 preferably is between 15 to 40 mm, more preferably between 20 to 38 mm, most preferably between 25 to 35 mm as measured from the first opening to the second opening when considering a cross section of the displacement element along longitudinal axis B.

The outer surface of the lower portion of the displacement means that is introduced into the first chamber, in particular the outer surface of the displacement element 109, may be shaped in different ways, for example in a substantially spherical, hemispherical, conical, truncated or cylindrical manner. Also the inner surface of the first chamber 103, in particular the inner surface of the closed lower end of the vessel 104 may have various shapes. As such, the inner surface may be, inter alia, substantially hemispherical, conical, truncated or cylindrical. Depending on the particular requirements, the above-mentioned shapes may be combined as desired. For example, rounded displacement means may be used with conical vessels and vice-versa.

FIGS. 8A-8E illustrate different embodiments of displacement means for devices according to the present invention, the forms of which may also be combined. As shown in these Figures, a gap G may be formed between the lower portion of the displacement means 105 and the interior wall of the vessel 104. More specifically, the gap G preferably is formed between the displacement element 109 and the vessel 104.

Figure 8A:
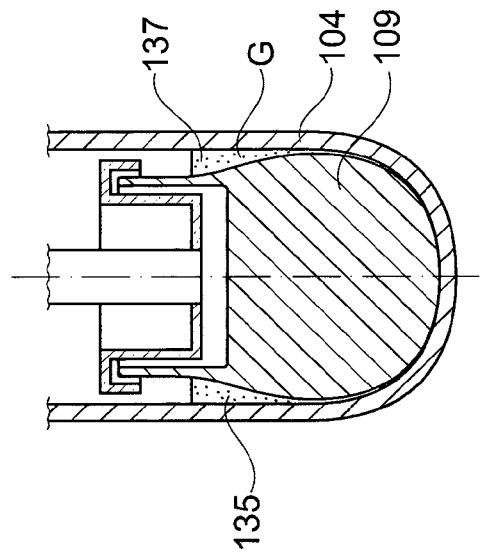
Figure 8B:
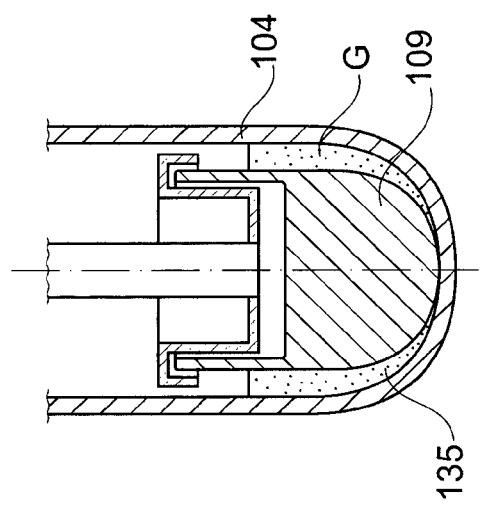
Figure 8C:
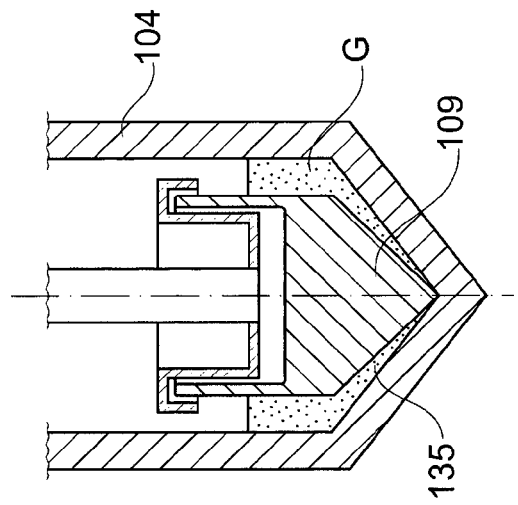

As shown in FIGS. 8A-8C, the gap G may be variable. In this case, the gap G preferably is formed such that a relatively large fraction of the first, seminal fluid received in the first chamber is displaced from the bottom of the first chamber proximate the first opening of the duct. The gap G may provide an enlarged collection space proximate the first opening. For this purpose, the width of the gap G preferably increases from a lower part towards an upper part of the first chamber 103 when the displacement means 105 is fully inserted. For example, the displacement element 109 may follow the inner surface of the first chamber at the bottom of the vessel 104 (i.e. at the closed lower end) and separate from the first chamber proximate the first opening 112 in order to form the collection space (see, for example, FIG. 8A).

Figure 8E:
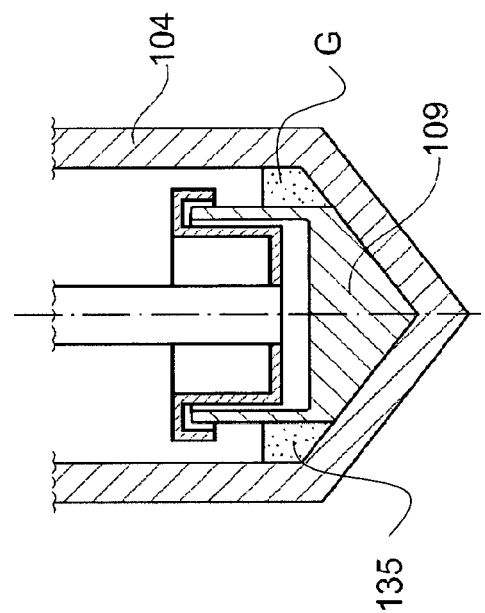
Figure 8D:
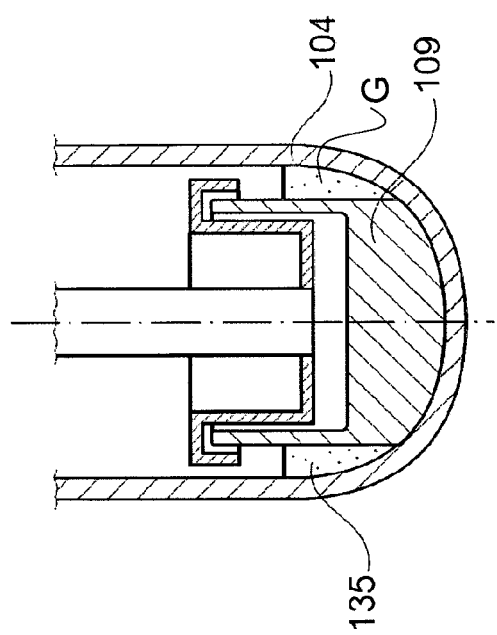

However, as shown in FIGS. 8D and 8E, the shape of the displacement element 109 may also match the shape of the lower end of the vessel 104. For example, both elements may have a generally hemispherical (FIG. 8D) or generally conical (FIG. 8E) shape along at least their contacting segments. As further apparent from FIGS. 8A-8E, the displacement means 109 may have different sizes and displacement volumes, the displacement means 109 of FIGS. 8D and 8E being somewhat "shorter" along the longitudinal axis B. It should be noted that any of displacement means described above (e.g., the displacement means illustrated in FIGS. 8A-8E) may be "shortened" or "elongated" in order to provide the displacement element 109 with a desired displacement volume and/or shape.

As further shown in FIGS. 9 and 10, the device may be provided with first and second scales 129, 131 for assessing the volume of the first, seminal fluid provided in the first chamber and the travel of the displacement means relative to the vessel 104, respectively. In the exemplary embodiment shown in FIGS. 9 and 10, the first scale 129 is provided on the vessel 104 and the second scale 131 is provided on the displacement means 105 (e.g., at an upper portion). However, the second scale may also be located on the vessel 104, for example, at an upper portion thereof. While the second scale 131 is described above as being located at the upper portion of the vessel 104 and the displacement means 105, it should be noted that the second scale may be located at any suitable height along the longitudinal axis of the device.

In embodiments of the invention, the second scale 131 may indicate the travel required for the displacement means dependant upon the volume of first, seminal fluid provided in the first chamber. Users of the device will then be able to assess the volume of first, seminal fluid in the first chamber by means of the first scale and, subsequently, the travel required for the displacement means on the second scale without having to perform intermediate steps or calculations.

In some cases, the distance to which the displacement means has to be inserted will not be inversely proportional to the volume received in the first chamber but, for example, correlate in a somewhat reciprocal manner. The distance between adjacent gradations of the second sale 131, therefore may vary and, for example, become smaller for larger volumes.

With the device of the present invention, the same volume of second fluid may be required, irrespectively of the volume of first, seminal fluid received in the first chamber. As shown in FIGS. 11A and 11B, the device 101 may also comprise a pipette 140. The pipette 140 may be adapted for being inserted into the shaft 123 and may contain a defined and/or fixed volume of second fluid 136, determined such that optimal wetting of the duct is ensured. Since the fluid level in the first chamber may be adjusted with the displacement means, this volume may be fixed, regardless of the volume of first, seminal fluid provided in the first chamber. Further, the pipette 140 may be configured to inject the second fluid 136 at a predetermined speed and/or with a predetermined pressure in order to prevent formation of air bubbles in the second fluid 136. The device 101 and the pipette 140 may be provided as a kit.

According to embodiments of the invention, the closure means (e.g., plug 127) may be inserted into the first chamber 103 after sealing it therewith. More specifically, the closure means may be inserted into the vessel 104 after sealing it, for example, at its open upper end.

As illustrated in FIG. 12A, the closure means may be configured such that they can be inserted a predetermined maximal depth into the vessel. By way of example, the plug 227 has a lower portion with a first diameter and an upper portion with a second diameter that is larger than the first diameter. Therefore, an abutment surface is formed that abuts the upper end of the side wall of the vessel 104 and prevents further insertion of the plug when the maximal depth is reached. The illustrative embodiment further comprises an optional screw cap 228 that is provided with an inner thread 229 in order to engage an attachment means 106 of the vessel 104. As shown, the attachment means 106 may be formed by an outer thread formed on the outer surface of the vessel's wall. It should be noted that also other plugs (e.g., a generally cylindrical plug having a diameter that corresponds to the inner diameter of the upper end of the vessel 104) may be employed. Such plugs may be affixed to the cap 228 or may be formed as separate components.

When the second chamber is filled in the way shown in FIG. 12B, with the level of the second fluid 136 being higher than the first opening of the duct, the positive pressure caused by inserting the plug 127, 227 into the vessel 104 may push a fixed volume of second fluid 136 located along the inner part of the duct proximate the second opening into the second chamber. As described above, the vessel 104 may be sealed thereafter, so that no additional fluid is drawn into the second chamber when the fluid contained therein is extracted.

FIGS. 13A-13E illustrate a device for spermatozoa selection 101 according to another embodiment of the present invention. In FIGS. 13A, 13B, and 13C, the selection device 101 is shown with the displacement means 105 fully introduced into the vessel 104 in plan, sectional and perspective views, respectively.

As shown in FIG. 13B, an ideal space S may be achieved between the first fluid 135 contained in the first chamber 103 and the opening of the duct leading to the second chamber 115 even if only small volumes of seminal fluid 135 are provided in the first chamber 103. In contrast, FIGS. 13D and 13E illustrate the selection device 101 with the displacement means 105 located in the upper part of the first chamber 103. As best shown in FIG. 13E, this configuration allows providing a relatively large volume of the first fluid 135 in the first chamber 103. Therefore, the device of FIGS. 13A-13E may provide the same functionality as the devices of FIGS. 3A-12B described above.

As further shown in FIGS. 13A-13E, the vessel 104 may be closed with a cap 328, which may be provided, for example, with a bayonet fit 329 in order to attach it to a corresponding attachment structure 306 of the vessel 104. It will be noted, however, that also other means may be used in this context, as, for example, a screw-on cap, a cap with a screw-on collar, or a cap with a snap fit.

The cap 328 may comprise vent holes 330. Preferably, the vent holes 330 can be closed by means of a plug 327, which is mounted on the cap 328 in the exemplary embodiment illustrated in these Figures. The plug 327 can be turned relatively to the cap 328 in order to close the vent holes 330 in an airtight manner. As such, the first chamber 103 may be sealed.

As shown in FIGS. 13B and 13E, the displacement means 105 may comprise a shaft 123 with an external threading 124. Correspondingly, a through-hole with an internal threading 324 may be formed in the cap, which through-hole may be used to centre the displacement means 105 in the vessel 104. By means of the interacting external and internal threading, the displacement means 105 with the second chamber 115 forming the displacement element may be lowered or raised in the vessel, thereby allowing a user to set the correct height of the displacement means 105 in accordance with the volume of first fluid 135 provided in the first chamber 103.

The vessel 104 of the device 101 of FIGS. 13A-13E is shown with a flat lower end and may be self-standing without the need of a support. However, the bottom of the vessel 104 may also be provided with other shapes, as discussed in detail above.

FIG. 14A illustrates the funnel structure 170 of the present invention in an upright position, such that the funnel can be used to fill liquids into a receptacle or vessel. The funnel structure 170 has a first circumferential wall 171 and a second circumferential wall 172, which both taper towards the inside of the funnel structure 170 (i.e., towards its central axis) in a downward direction. As shown, the first circumferential wall 171 may form an outer funnel and the second circumferential wall may form an inner funnel with respect to said outer funnel. The inner and outer funnels may have generally conical shapes along at least a segment.

The first and second circumferential walls may be connected by an upper wall 173. Preferably, a recuperation compartment 179 is formed between the first and second circumferential walls. The upper end of the recuperation compartment may be closed by upper wall 173 and may be open in a downward direction when the funnel structure 170 is positioned in an upright manner. One, several or all of the walls of the funnel structure may be formed from polymeric materials or glass. The walls may be formed integrally.

Further, the funnel structure 170 comprises an inlet opening 175 and an outlet opening 177. The outlet opening 177 preferably has a smaller cross-sectional area than the inlet opening 175 and preferably is disposed below the inlet opening 175 when the funnel structure 170 is in the upright position, as shown in FIG. 14A. An intermediate opening 176 may be disposed between the inlet opening 175 and the outlet opening 177.

Preferably, the inlet opening 175 is formed at the upper end of the second circumferential wall 172 and the intermediate opening 176 is formed at the lower end of the second circumferential wall 172. The outlet opening 177 preferably is formed at the lower end of the first circumferential wall 171.

The funnel structure 170 may be provided with an attachment structure 174 for attaching the funnel to a vessel. In the illustrated example, the attachment structure 174 is provided on a cylindrical protrusion with an internal thread. The vessel 104 may be inserted into the cylindrical protrusion in order to prevent contamination of the vessel's inner walls. However, also other types of connectors and/or attachment structures may be provided, as appropriate.

As shown in FIG. 14A, the funnel structure may also comprise an optional air vent 178 that fluidly connects the interior of the vessel 104 and the environment. In the shown embodiment, the air vent 178 provides a fluid connection between the interior of the vessel 104 and the recuperation compartment 179. The air vent 178 may be provided by a hole traversing the first circumferential wall 171.

As further shown in FIG. 14A, the funnel structure may be attached to the vessel 104 of the selection device and used in combination therewith. The vessel 104 may be provided with attachment means 106 for this purpose. The attachment means 106 may be configured to engage the attachment structure 174 of the funnel structure 170. As illustrated, the attachment means 106 may be provided proximate the upper opening of the vessel 104 according to embodiments of the invention.

The vessel 104 may be inserted into a stand 180 in order to maintain it in an upright position or may be self standing.

FIG. 14B illustrates the functional principle of the funnel structure 170. When the vessel 104 and the funnel structure 170 are disposed in a horizontal position, knocked over or turned around, most or all of the liquid (e.g., the seminal fluid 135) that is contained in the vessel 104 and flows out through the outlet opening 177 of the funnel structure 170 is captured in the recuperation compartment 179. Therefore, contamination of the liquid flowing out of the vessel 104 is prevented and the liquid may be filled back into the vessel 104, e.g., by holding the funnel structure 170 and the vessel 104 in the upright manner shown in FIG. 14A.

Moreover, the attachment structure 174 preferably is configured to provide a leak-proof attachment with the vessel 104, such that, when the vessel 104 is disposed in a horizontal position, knocked over and/or turned upside-down, the liquid 135 remaining in the vessel 104 does not leak through the upper opening of the vessel 104. However, the vessel 104, the funnel structure 170 and/or the stand 180 may also be configured such that the vessel's bottom is below its opening when the vessel is knocked over and/or lies horizontally. In this case, a leak proof seal between the attachment structure 174 of the funnel structure 170 and the attachment means 106 of the vessel 104 may not be required.

FIGS. 15A and 15B show a further embodiment of a funnel structure in accordance with the present invention in plan and sectional views, respectively. The funnel structure 470 is similar to the funnel structure 170 of FIGS. 14A and 14B and the same reference numbers are used for some of the elements that are alike or similar. In this context, reference is made to the description of funnel structure 170 provided above in order to avoid repetitions.

As can be seen from FIGS. 15A and 15B, the funnel structure 470 is configured with attachment means in the form of a bayonet fit 474 that cooperates with the corresponding attachment section 306 provided to the vessel. Accordingly, the funnel structure 470 is configured for use with the selection device 101 of FIGS. 13A-13E and the funnel structure may be attached to the vessel by the same mechanism than the cap 327.

Finally, FIG. 16 shows a table in which the spermatozoa concentration achieved is reported for selections performed after letting the ejaculate rest for 15 to 30 min. and without such resting period. For the purposes of this study, the ejaculate of four different Patients (Patients A-D) has been processed with the device of the present invention. The "Final concentration", indicated in the Table in millions of spermatozoa per ml, reports the concentration achieved in the second fluid after selection, which is the fluid from which the spermatozoa are then retrieved for in-vitro fertilization. Further separation steps are not required. While a different sperm sample has been used for each measurement, all patients enrolled have been shown—in several previous studies—to provide sperm samples of very similar volume and quality after an abstinence period of 3 days.

As can be observed, substantial improvements have been achieved in all cases in which the semen sample is used directly after ejaculation, including a tenfold higher concentration of spermatozoa. Conversely, a considerably lower concentration (up to ten times lower) is yielded when waiting for 15 to 30 min., letting the ejaculate rest in order to liquefy it. It is, therefore, preferred to introduce semen samples into the selection device of the present invention directly after ejaculation, without resting periods and/or the use of additional vessels.

As will be acknowledged by the skilled person in view of the description provided above, the present invention provides improved selection devices and methods that can be used with varying volumes of seminal fluid. In particular, the device may be used for seminal fluid volumes of less than 1 ml or less than 0.5 ml without requiring dilution. The time required for separating such sperm samples may be reduced significantly, thereby decreasing chemical stress due to contact with atmospheric $O_2$. Further, less handling steps are required and mechanical stress is reduced also.

Since the first chamber may be sealed relative to the environment, contamination of the collected sample by spermatozoa with strand breaks and/or low motility is prevented. Moreover, exposure of spermatozoa to oxygen before, during and/or after the selection procedure is reduced further.

Additionally, the same amount of medium may be used irrespectively of the volume of seminal fluid received in the first chamber. Thus, handling of the device is simplified and repeatable results are obtained more easily. Wetting of the fluid connection is improved, e.g., when using the pipette described above for injecting the medium, which may also lead to better results when performing the selection procedure.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above.

The invention claimed is:

1. A device for spermatozoa selection having a longitudinal axis, an upper end, and a lower end, the device comprising:
   a first chamber configured to receive a first, seminal fluid; and
   a displacement element configured to be inserted within the first chamber, the displacement element defining a second chamber configured to receive a second fluid, the second chamber being in fluid communication with the first chamber by at least one duct having a first opening to the first chamber and a second opening to the second chamber,
   wherein the displacement element is adapted to displace at least some of the first, seminal fluid towards the first opening;
   wherein the duct is configured to provide a fluid communication between the first chamber and the second chamber to allow spermatozoa to move from the first chamber to the second chamber;
   wherein, in a cross section along the longitudinal axis of the device, the duct comprises at least a first segment that extends in a first direction having a directional component towards the upper end of the device and at least a second segment that extends in a second direction having a directional component towards the lower end of the device; and
   wherein the first segment is prior to the second segment when following the duct from the first opening to the second opening.

2. Device according to claim 1, wherein the first chamber is provided by a vessel with a closed lower end.

3. Device according to claim 1, wherein the displacement element is slidably received in the first chamber.

4. Device according to claim 1, wherein the displacement element is adapted to displace the first, seminal fluid such that the upper surface of the first, seminal fluid is arranged at a predetermined distance from the first opening.

5. Device according to claim 1, wherein the displacement means comprises a displacement body.

6. Device according to claim 1, wherein the displacement element comprises a shaft for manipulating the displacement element, wherein the shaft is hollow and opens out into the second chamber.

7. Device according to claim 1, wherein the second chamber is formed in the displacement element.

8. Device according to claim 1, wherein the duct has a cross section of an inverted U, a first leg of said U extending to the first chamber and a second leg of said U extending to the second chamber.

9. Device according to claim 1, wherein the displacement element comprises an upwardly extending rim and wherein the shaft is connected with a ring-shaped cover, wherein the duct is formed between the rim and the cover.

10. Device according to claim 1, wherein the vessel is provided with a first scale for assessing a volume of the first, seminal fluid in the first chamber.

11. Device according to claim 10, comprising a second scale for assessing travel of the displacement element.

12. Device according to claim 11, wherein the second scale indicates the required travel of the displacement element dependent upon the volume indicated by the first scale.

13. Device according to claim 1, further comprising a plug for sealing the first chamber relative to the environment.

14. Method for selecting mobile cells using the device of claim 1 including the steps of:
   (a) providing a first fluid comprising motile cells in the first chamber;
   (b) providing a buffer medium in the second chamber; and
   (c) connecting the first chamber and the second chamber by a liquid connection; and
   (d) displacing at least some of the first fluid towards, proximate or to the first opening of the duct with the displacement element.

15. The method of claim 14, wherein the first fluid is substantially unmixed human ejaculate.

16. Device according to claim 1, wherein the first chamber is provided by a vessel, and a gap is formed between the displacement element and an interior wall of the vessel.

* * * * *